(12) United States Patent
Kim et al.

US010696990B2

(10) Patent No.: US 10,696,990 B2
(45) Date of Patent: Jun. 30, 2020

(54) VARIANT OF O-PHOSPHOSERINE EXPORTER AND METHOD OF PRODUCING O-PHOSPHOSERINE, CYSTEINE, AND ITS DERIVATIVES USING THE SAME

(71) Applicant: CJ CHEILJEDANG CORPORATION, Seoul (KR)

(72) Inventors: Sol Kim, Suwon-si (KR); Min Gyeong Kang, Seoul (KR); In Hwa Yoo, Suwon-si (KR); Jong Hyun Kim, Anyang-si (KR); Hye Won Kim, Seongnam-si (KR)

(73) Assignee: CJ CHEILJEDANG CORPORATION, Seoul (KR)

(*) Notice: Subject to any disclaimer, the term of this patent is extended or adjusted under 35 U.S.C. 154(b) by 0 days.

(21) Appl. No.: 15/758,248

(22) PCT Filed: Sep. 9, 2016

(86) PCT No.: PCT/KR2016/010168
§ 371 (c)(1),
(2) Date: Mar. 7, 2018

(87) PCT Pub. No.: WO2017/043915
PCT Pub. Date: Mar. 16, 2017

(65) Prior Publication Data
US 2019/0233859 A1    Aug. 1, 2019

(30) Foreign Application Priority Data

Sep. 11, 2015 (KR) .................. 10-2015-0129127

(51) Int. Cl.
| | | |
|---|---|---|
| *C12P 13/12* | (2006.01) | |
| *C12N 15/00* | (2006.01) | |
| *C12N 1/20* | (2006.01) | |
| *C07H 21/02* | (2006.01) | |
| *C07K 1/00* | (2006.01) | |
| *C07K 14/245* | (2006.01) | |
| *C12N 9/10* | (2006.01) | |
| *C12N 9/16* | (2006.01) | |
| *C12N 15/70* | (2006.01) | |

(52) U.S. Cl.
CPC ............ *C12P 13/12* (2013.01); *C07K 14/245* (2013.01); *C12N 9/10* (2013.01); *C12N 9/16* (2013.01); *C12N 15/70* (2013.01)

(58) Field of Classification Search
None
See application file for complete search history.

(56) References Cited

U.S. PATENT DOCUMENTS 7,662,943 B2    2/2010 Park et al.
8,557,549 B2    10/2013 Chang et al.

| 10,323,262 B2 * | 6/2019 | Kim ...................... C12P 13/06 |
| 2003/0008358 A1 | 1/2003 | Suga et al. |
| 2012/0190081 A1 | 7/2012 | Chang et al. |

FOREIGN PATENT DOCUMENTS

| EP | 0885962 B1 | 4/2005 |
| KR | 100620092 B1 | 9/2006 |
| KR | 10-2012-0041115 | 4/2012 |
| KR | 10-2013-0068135 | 6/2013 |
| KR | 101381048 B1 | 4/2014 |
| KR | 10-2014-0133754 | 11/2014 |
| KR | 10-2014-0133751 | 2/2015 |
| WO | 2014/182119 A1 | 11/2014 |

OTHER PUBLICATIONS

NCBI, GenBank accession No. EEH71170.2, dated Sep. 11, 2012. [Cited in an International Search Report and Written Opinion in International Application No. PCT/KR2016/010168, dated Dec. 26, 2016.].
International Search Report and Written Opinion in International Application No. PCT/KR2016/010168, dated Dec. 26, 2016. [Cited in an International Search Report and Written Opinion in International Application No. PCT/KR2016/010168, dated Dec. 26, 2016.].
Ehrhardt et al., "Optimization of Cis-Acting Elements for Gene Expression form Nonviral Vectors In Vivo," Human Gene Therapy, 14: 215-225 (Feb. 2003).
Chen et al., "Silencing of episomal transgene expression by plasmid bacterial DNA elements in vivo," Gene Therapy, 11, pp. 856-864 (2004).
Hayes, "Transposon-Based Strategies Formicrobial Functional Genomics and Proteomics", Annu. Rev. Genet. 2003. 37:3-29, doi: 10.1146/annurev.genet.37.110801.142807, First published online as a Review in Advance on Sep. 8, 2003.
Rest et al., "A heat shock following electroporation induces highly efficient transformation of Corynebacterium glutarnicum with xenogeneic plasmid DNA", Appl Microbiol Biotechnol (1999) 52: 541-545.
Wada et al., Metabolic pathways and biotechnological production of L-cysteine, Appl Microbiol Biotechnol (2006) 73:48-54.
Peters-Wendisch et al., 3-Phosphoglycerate dehydrogenase from Corynebacterium glutamicum : the C-terminal domain is not essential for activity but is required for inhibition by L-serine, Appl Microbiol Biotechnol (2002) 60:437-441.

(Continued)

*Primary Examiner* — Yong D Pak
(74) *Attorney, Agent, or Firm* — Keith G. Haddaway; Venable LLP; Miguel A. Lopez

(57) ABSTRACT

The present disclosure relates to a novel polypeptide having O-phosphoserine (OPS) exporting activity, a polynucleotide encoding the polypeptide, a microorganism expressing the polypeptide, a method for producing OPS using the microorganism, and a method for producing cysteine or a derivative thereof comprising reacting the O-phosphoserine produced by the same with a sulfide, in the presence of O-phosphoserine sulfhydrylase (OPSS) or a microorganism expressing the same.

10 Claims, No Drawings
Specification includes a Sequence Listing.

(56) References Cited

OTHER PUBLICATIONS

Grant et al., "Role of an Interdomain Gly-Gly Sequence at the Regulatory-Substrate Domain Interface in the Regulation of *Escherichia coli*. D-3-Phosphoglycerate Dehydrogenase†", Biochemistry 2000, 39, 7316-7319.

Mino et al, A novel O-phospho-L-serine sulfhydrylation reaction catalyzed by O-acetylserine sulfhydrylase from Aeropyrum pemix K, FEBS Letters 551 (2003) 133/\138.

Burns et al., Reconstitution of a New Cysteine Biosynthetic Pathway in Mycobacterium tuberculosis, J. Am. Chem. Soc. 2005, 127, 11602-11603.

Grant et al., The Contribution of Adjacent Subunits to the Active Sites of D-3-Phosphoglycerate Dehydrogenase*, The Journal of Biological Chemistry, vol. 274, No. 9, Issue of Feb. 26, pp. 5357-5361, 1999.

Grant et al., "Amino Acid Residue Mutations Uncouple Cooperative Effects in *Escherichia coli* D-3—Phosphoglycerate Dehydrogenase*", The Journal of Biological Chemistry, vol. 276, No. 21, Issue of May 25, pp. 17844-17850, 2001.

Sauer et al., The Soluble and Membrane-bound Transhydrogenases UdhA and PritAB Have Divergent Functions in NADPH Metabolism of *Escherichia coil**, The Journal of Biological Chemistry, vol. 279, No. 8, Issue of Feb. 20, pp. 6613-6619, 2004.

Yew et al., CpG-Depleted Plasmid DNA Vectors with Enhanced Safety and Long-Term Gene Expression in Vivo, Molecular Therapy vol. 5, No, 6, Jun. 2002, pp. 731-738.

\* cited by examiner

VARIANT OF O-PHOSPHOSERINE EXPORTER AND METHOD OF PRODUCING O-PHOSPHOSERINE, CYSTEINE, AND ITS DERIVATIVES USING THE SAME

This application is a U.S. National Stage Application under 35 U.S.C. § 371 of PCT/KR2016/010168, filed on Sep. 9, 2016, the entire content of which is hereby incorporated by reference, and claims the benefit of Korean Patent Application No. 10-2015-0129127, filed Sep. 11, 2015.

SEQUENCE LISTING

The instant application contains a Sequence Listing which has been submitted electronically in ASCII format and is hereby incorporated by reference in its entirety. Said ASCII copy, created on Jun. 18, 2018, is named Sequence Listing 15758248.txt and is 41,906 bytes in size.

TECHNICAL FIELD

The present disclosure relates to a novel modified polypeptide having the activity of exporting O-phosphoserine (OPS), a precursor of L-cysteine, a polynucleotide encoding the polypeptide, an O-phosphoserine-producing microorganism expresses the polypeptide, a method for producing O-phosphoserine using the microorganism, and a method for producing cysteine or a derivative thereof comprising reacting the O-phosphoserine produced by the above method with a sulfide, in the presence of O-phosphoserine sulfhydrylase (OPSS) or a microorganism expressing the same.

BACKGROUND ART

L-cysteine, an amino acid playing an important role in sulfur metabolism in all living organisms, is used not only in the synthesis of biological proteins such as hair keratin, glutathione, biotin, methionine, and other sulfur-containing metabolites, but also as a precursor for biosynthesis of coenzyme A.

Known methods of producing L-cysteine using microorganisms include: 1) a method of biologically converting D,L-2-aminothiazoline-4-carboxylic acid (D,L-ATC) to L-cysteine using microorganisms, 2) a method of producing L-cysteine by direct fermentation using *E. coli* (EP0885962B; Wada M and Takagi H, Appl. Microbiol. Biochem., 73:48-54, 2006), and 3) a method of producing O-phosphoserine by fermentation using microorganisms, and converting O-phosphoserine into L-cysteine by reacting O-phosphoserine with a sulfide under the catalytic action of O-phosphoserine sulfhydrylase (Korean Patent No. 1381048). In particular, for the production of cysteine by the method 3) at high yield, the precursor, O-phosphoserine, should be produced in excessive amounts.

In this regard, the present inventors have made extensive efforts to discover an appropriate export factor that can smoothly export O-phosphoserine produced in an O-phosphoserine-producing microorganism from cells. Specifically, the present inventors have discovered an RhtB variant as a protein having O-phosphoserine-exporting activity (Korean Patent Application Publication No. 10-2014-0133751) and a novel O-phosphoserine-exporter (Korean Patent Application Publication No. 10-2014-0133754), and have confirmed that O-phosphoserine concentration increased when these proteins were activated in an O-phosphoserine-producing microorganism.

DISCLOSURE

Technical Problem

Under these circumstances, the present inventors have made efforts to discover O-phosphoserine exporters which can increase O-phosphoserine production with improved O-phosphoserine-exporting activity, and develop variants thereof, and as a result, have succeeded in developing an O-phosphoserine exporter variant which can effectively export O-phosphoserine from an O-phosphoserine-producing microorganism, thereby completing the present disclosure.

Technical Solution

It is therefore an object of the present disclosure to provide a polypeptide having O-phosphoserine (OPS) exporting activity.

Another object of the present disclosure is to provide a polynucleotide encoding the polypeptide.

Still another object of the present disclosure is to provide an O-phosphoserine producing microorganism of the genus *Escherichia* expressing the polypeptide.

Still another object of the present disclosure is to provide a method for producing O-phosphoserine comprising culturing the microorganism producing O-phosphoserine.

Still another object of the present disclosure is to provide a method for producing cysteine or a derivative thereof comprising reacting the O-phosphoserine produced above with a sulfide, in the presence of O-phosphoserine sulfhydrylase or a microorganism expressing the same.

Advantageous Effects of the Invention

The novel modified polypeptide represented by an amino acid sequence selected from the group consisting of SEQ ID NO: 1, SEQ ID NO: 3, and SEQ ID NO: 5 of the present disclosure has an excellent OPS-exporting activity. Accordingly, when the novel polypeptide of the present disclosure is applied to a microorganism producing OPS, it can lead to high-yield production of OPS, and also effective production of L-cysteine by the same.

BEST MODE

The present disclosure, in order to achieve the above objects, is described in detail herein below.

In an aspect, the present disclosure relates to a polypeptide having O-phosphoserine (OPS) exporting activity, which is represented by an amino acid sequence selected from the group consisting of SEQ ID NO: 1, SEQ ID NO: 3, and SEQ ID NO: 5.

In another aspect, the present disclosure relates to the use of the polypeptide, which is represented by an amino acid sequence selected from the group consisting of SEQ ID NO: 1, SEQ ID NO: 3, and SEQ ID NO: 5, for exporting O-phosphoserine.

As used herein, the term "O-phosphoserine" (hereinafter "OPS") refers to a phosphoric acid ester of serine which serves as a constituting component for many proteins. In particular, the OPS is a precursor of L-cysteine and can be converted to cysteine by reacting with a sulfide under the catalytic action of OPS sulfhydrylase (hereinafter "OPSS").

As used herein, the term "a polypeptide having OPS-exporting activity" refers to a membrane protein which has the activity of exporting the OPS in a cell to the outside of the cell, and specifically, it may refer to a membrane protein derived from *E. coli*. The polypeptide of the present disclosure having OPS-exporting activity may be a YhhS major facilitator superfamily (MFS) transporter or a variant thereof. Specifically, the polypeptide may be a variant of the YhhS MFS transporter exhibiting improved activity compared to that of wild type YhhS MFS transporter, which has been identified as a protein having OPS-exporting activity in *E. coli*, where growth inhibition is released in a condition where an excess amount of OPS is present.

Specifically, the polypeptide may be represented by an amino acid sequence selected from the group consisting of SEQ ID NO: 1, SEQ ID NO: 3, and SEQ ID NO: 5, and may include, without limitation, membrane proteins having a sequence homology to the above sequences of at least 70%, specifically at least 80%, more specifically at least 90%, and even more specifically at least 95%, as long as they have the OPS-exporting activity, which is substantially the same as or equivalent to that of the polypeptide. Additionally, it is obvious that polypeptide variants in which part of the sequence is deleted, modified, substituted, or inserted should be included in the scope of the present disclosure, as long as they are amino acid sequences having these homologies and the OPS-exporting activity.

As used herein, the term "homology" refers to a degree of identity or equivalence with a given polypeptide sequence or polynucleotide sequence which may or may not share a common evolutionary origin, and may be indicated as a percentage. As used herein, the homologous sequence having the same or similar activity with the given polypeptide sequence or polynucleotide sequence may be indicated in terms of "% homology". The % homology may be confirmed using standard software for calculating parameters such as score, identity, and similarity, specifically, BLAST 2.0, or by comparing sequences via southern hybridization experiments under defined strict conditions, and the defined strict hybridization conditions may be determined by a method known to a skilled person in the art (e.g., Sambrook et al., 1989, infra). In an exemplary embodiment of the present disclosure, when two different amino acid sequences have at least 21% of polypeptide sequence matching for a given length of an amino acid sequence (specifically, at least about 50%, and in particular, about 75%, 90%, 95%, 96%, 97%, or 99%), they are "substantially the same" or "substantially same".

In still another aspect, the present disclosure provides a polynucleotide encoding the polypeptide having O-phosphoserine (OPS) exporting activity, i.e., a polynucleotide encoding the YhhS MFS transporter polypeptide variant. Specifically, the present disclosure provides a polynucleotide encoding the polypeptide having O-phosphoserine exporting activity, represented by an amino acid sequence selected from the group consisting of SEQ ID NO: 1, SEQ ID NO: 3, and SEQ ID NO: 5.

The OPS, YhhS MFS transporter, etc., are the same as described above.

As used herein, the term "polynucleotide" refers to a polymer of nucleotides, wherein nucleotide units are connected in a long chain-like manner by covalent bonds, and it generally refers to a DNA or RNA strand having a certain minimum length.

A polynucleotide sequence of the polypeptide having OPS-exporting activity may include a polynucleotide sequence encoding an amino acid sequence selected from the group consisting of SEQ ID NO: 1, SEQ ID NO: 3, and SEQ ID NO: 5. Considering the codons preferred by organisms to express the polypeptide based on the genetic code degeneracy, various modifications on the polynucleotide may be executed on the coding region within the scope not changing the amino acid sequence of the polypeptide. The polynucleotide sequence may include, for example, the polynucleotide sequences selected from the group consisting of SEQ ID NO: 2, SEQ ID NO: 4, and SEQ ID NO: 6. Additionally, the polynucleotide sequence may include nucleotide sequences having a sequence homology of 70% or higher, specifically 80% or higher, more specifically 90% or higher, even more specifically 95% or higher, and most specifically 98% or higher, to the above sequences, which are encoding polypeptides substantially having OPS-exporting activity. Additionally, it is obvious that polypeptide variants in which part of the sequence is deleted, modified, substituted, or inserted should be included in the scope of the present disclosure.

In still another aspect, the present disclosure provides a microorganism producing the polypeptide having an O-phosphoserine exporting activity, i.e., an OPS-producing microorganism expresses YhhS MFS transporter polypeptide variants, and specifically, a microorganism of the genus *Escherichia*.

In still another aspect, the present disclosure provides a use of the polypeptide having the O-phosphoserine exporting activity, i.e., an OPS production use of the microorganism expresses the YhhS MFS transporter polypeptide variants, and specifically, a microorganism of the genus *Escherichia*.

In the present disclosure, OPS, YhhS MFS transporters, etc. are the same as described above.

As used herein, the term "an OPS-producing microorganism" refers to a prokaryotic or eukaryotic microorganism strain capable producing OPS in vivo, and specifically, a microorganism which can accumulate OPS in a medium or within the microorganism by genetic manipulation or natural mutation.

Specifically, the microorganism is not particularly limited, but may be any prokaryotic or eukaryotic microorganism that can express the polypeptide selected from the group consisting of SEQ ID NO: 1, SEQ ID NO: 3, and SEQ ID NO: 5, and in particular, may be a prokaryotic microorganism, e.g., microbial strains belonging to the genus *Escherichia*, the genus *Erwinia*, the genus *Serratia*, the genus *Providencia*, the genus *Corynebacterium* and the genus *Brevibacterium*, and specifically, a microorganism belonging to the genus *Escherichia*, e.g., *E. coli*, but is not limited thereto.

As used herein, the term "expression" may be achieved by transformation using a recombinant vector, which operably includes the polynucleotide encoding the polypeptide of the present disclosure, or by inserting the polynucleotide encoding the polypeptide into chromosome, but is not limited thereto.

As used herein, the term "transformation" refers to a process of introducing a vector including a polynucleotide encoding a target protein into a host cell, thereby enabling the expression of the polynucleotide encoded by the protein in the host cell. For the transformed polynucleotide, it does not matter whether it is inserted into the chromosome of a host cell and located therein or located outside the chromosome, as long as it can be expressed in the host cell. Additionally, the polynucleotide includes DNA and RNA which encode the target protein. The polynucleotide may be inserted in any form insofar as it can be introduced into a host cell and expressed therein. For example, the polynucleotide may be introduced into a host cell in the form of an expression cassette, which is a genetic construct including all essential elements required for self-expression, but is not limited thereto. The expression cassette may conventionally include a promoter operably connected to the polynucleotide, a transcription termination signal, a ribosome-binding domain, and a translation termination signal. The expression cassette may be in the form of an expression vector capable of self-replication. Additionally, the polynucleotide may be introduced into a host cell as it is and operably connected to a sequence essential for its expression in the host cell.

Additionally, as used herein, the term "operably connected" refers to a functional connection between a promoter sequence, which initiates and mediates the transcription of the polynucleotide encoding the target protein of the present disclosure, and the above gene sequence.

As used herein, the term "vector" refers to any mediator for cloning and/or transfer of a nucleotide sequence into a host cell. The vector may be a replicon to which a different DNA fragment can bind, leading to replication of a combined fragment. As used herein, the term "replicon" refers to any genetic unit that functions as a self-unit for DNA replication, i.e., those which can be replicated by self-regulation (e.g., plasmids, phages, cosmids, chromosomes, and viruses). The vector may include viral and non-viral mediators for in vivo, ex vivo, or in vitro introduction of a nucleotide into a host cell, and may also include minicircle DNA. For example, the vector may include plasmids which do not have any bacterial DNA sequence. The removal of bacterial DNA sequences which are rich in CpG domain have been conducted to reduce the expression silencing of a transferred gene and inducing constitutive expression compared to the plasmid DNA vector (e.g., Ehrhardt, A. et al. (2003) HumGene Ther 10: 215-25; Yet, N. S. (2002) MoI Ther 5: 731-38; Chen, Z. Y. et al. (2004) Gene Ther 11: 856-64). Additionally, the vector may include transposons (*Annu Rev Genet.* 2003; 37: 3-29.) or artificial chromosomes. Specifically, pACYC177, pACYC184, pCL1920, pECCG117, pUC19, pBR322, and pMW118 vectors, and vectors with modified promoters thereof may be used, but are not limited thereto.

The vector may be a DNA construct including the polynucleotide sequence of the polynucleotide encoding the target protein, which is operably connected to a suitable regulation sequence so that the target protein can be expressed in an appropriate host. The regulation sequence includes a promoter capable of initiating transcription, a random operator sequence for regulation of the transcription, a sequence encoding a suitable mRNA ribosome-binding domain, and a sequence for regulation of transcription and translation. The vector, after being transformed into an appropriate host cell, may be replicated or function irrespective of the host genome, or may be integrated into the host genome itself.

The vector used in the present disclosure may not be particularly limited as long as the vector is replicable in the host cell, and any vector known in the art may be used. Examples of the vector may include natural or recombinant plasmids, cosmids, viruses, and bacteriophages. For example, as a phage vector or cosmid vector, pWE15, M13, λMBL3, λMBL4, λIXII, λASHII, λAPII, λt110, λt11, Charon4A, Charon21A, etc. may be used, but is not limited thereto; and as a plasmid vector, those based on pBR, pUC, pBluescriptH, pGEM, pTZ, pCL, pET, etc. may be used, but is not limited thereto.

Additionally, in the OPS-producing microorganism, the activity of phosphoserine phosphatase (SerB) may be further weakened compared to its endogenous activity.

The SerB has an activity of converting OPS to L-serine, and thus the microorganism modified to reduce the SerB activity has the property of accumulating OPS therein, thus being useful for the production of OPS. The SerB may be a protein having an amino acid sequence represented by SEQ ID NO: 16, but is not limited thereto. Additionally, the SerB may include an amino acid sequence having a sequence identity of 80% or higher, specifically 90% or higher, more specifically 95% or higher, and even more specifically 99% or higher, as long as it shows the SerB activity, but is not limited thereto. Additionally, the polynucleotide sequence encoding SerB may have a polynucleotide sequence encoding the amino acids represented by SEQ ID NO: 16.

Considering the codons preferred by organisms to express the polypeptide based on the genetic code degeneracy, various modifications on the polynucleotide may be executed on the coding region within the scope not changing the amino acid sequence of the polypeptide. The polynucleotide sequence may include an amino acid sequence, e.g., that represented by SEQ ID NO: 17, and may include nucleotide sequences having a sequence homology of 80% to the sequence, and specifically 90% or higher, but is not limited thereto.

As used herein, the term "weakness of activity" refers to a reduction of the activity of a protein compared with that possessed by a microorganism in its wild-type state or before modification, and it also includes when the activity is eliminated.

The weakness is a concept referring to a case when the activity of a protein is reduced or eliminated compared to endogenous activity of the microorganism due to a modification in the protein-encoding gene, etc.; a case when the level of protein expression is lower than that of the wild-type strain of the microorganism due to inhibition of expression or inhibition of translation of the gene encoding the same, etc.; a case when the gene is not expressed at all; and a case when the gene is expressed but exhibits no activity.

The weakness of a protein activity may be achieved by various methods well known in the art. Examples of the methods may include a method of substituting the gene encoding the protein on the chromosome with a gene mutated so that the enzyme activity can be reduced, including the case when the protein activity is eliminated; a method of modifying the expression regulation sequence of the gene encoding the protein; a method of deleting part or the entirety of a gene encoding the protein on the chromosome; a method of introducing an antisense oligonucleotide (e.g., antisense RNA), which inhibits the translation from the mRNA into a protein via a complementary binding to the transcript of the gene on the chromosome; a method of making the attachment of a ribosome impossible by forming a secondary structure by artificially adding a complementary sequence to the Shine-Dalgarno (SD) sequence on the front end of the SD sequence of the gene encoding the protein; a method of reverse transcription engineering (RTE), which adds a promoter so as to be reversely transcribed on the 3' terminus of the open reading frame (ORF) of the corresponding sequence, etc., and also include a combination thereof, but are not particularly limited thereto.

Specifically, the method of deleting part or the entirety of a gene encoding the protein may be executed by replacing the polynucleotide encoding the endogenous target protein within the chromosome with a polynucleotide or a marker gene having a partially deleted nucleic acid sequence, and using a vector for inserting chromosomes into bacteria. In an exemplary embodiment, the gene may be deleted by homologous recombination. Additionally, as used herein, the term "part", although it may vary depending on the kinds of polynucleotide, may specifically refer to 1 nucleotide to 300 nucleotides, more specifically 1 nucleotide to 100 nucleotides, and even more specifically 1 nucleotide to 50 nucleotides, but is not particularly limited thereto.

Additionally, the method of modifying the expression regulation sequence may be performed by inducing a modification in the expression regulation sequence via deletion, insertion, conservative substitution, non-conservative substitution, or a combination thereof so as to further weaken the activity of the expression regulation sequence; or by replacing the sequence with a nucleic acid sequence having a weaker activity. The expression regulation sequence includes a promoter, an operator sequence, a sequence encoding a ribosome-binding domain, and a sequence for regulating transcription and translation.

Additionally, the method of modifying the gene sequence may be performed by inducing a modification in the gene sequence via deletion, insertion, conservative substitution, non-conservative substitution, or a combination thereof so as to further weaken the activity of the protein; or by replacing the sequence with a gene sequence improved to have a weaker activity or a gene sequence improved to have no activity at all.

Particularly, the weakness of the activity of SerB in the present disclosure may be achieved by at least one method selected from the group consisting of a method of removing the activity of SerB; a method of substituting the SerB-encoding gene on the chromosome with a gene mutated so that the SerB activity can be reduced; a method of introducing a modification in the expression regulation sequence of the SerB-encoding gene on the chromosome; a method of substituting the expression regulation sequence of the SerB-encoding gene with a sequence having a weaker activity; a method of deleting the SerB-encoding gene on the chromosome and a method of introducing an antisense oligonucleotide, which inhibits the translation from the mRNA into a protein via a complementary binding to the transcript of the SerB-encoding gene on the chromosome; a method of making the attachment of a ribosome impossible by forming a secondary structure by artificially adding a complementary sequence to the Shine-Dalgarno (SD) sequence on the front end of the SD sequence of the gene encoding the protein; a method of making the attachment of a ribosome impossible by forming a secondary structure by artificially adding a complementary sequence to the Shine-Dalgarno (SD) sequence on the front end of the SD sequence of the SerB-encoding gene; and a method of reverse transcription engineering (RTE), which adds a promoter so as to be reversely transcribed on the 3' terminus of the open reading frame (ORF) of the corresponding sequence.

Additionally, the OPS-producing microorganism may be one in which the activity of phosphoglycerate dehydrogenase (SerA) or phosphoserine aminotransferase (SerC) is further enhanced compared to their respective endogenous activity.

The SerA is a protein capable of converting 3-phosphoglycerate into 3-phospho-hydroxypyruvate. The SerA may be used as form of a wild-type or a variant where the feedback inhibition on serine is released. Additionally, the SerC is a protein capable of converting 3-phospho-hydroxypyruvate to OPS. Accordingly, any microorganism with enhanced SerA and/or SerC activities may be effectively used as an OPS-producing microorganism.

The SerA may have an amino acid sequence represented by SEQ ID NO: 18 or SEQ ID NO: 19, although it is not limited thereto. The SEQ ID NO: 18 is a sequence of wild-type SerA, and SEQ ID NO: 19 is a sequence of a variant where the feedback inhibition on serine is released. Additionally, those amino acid sequences which have at least 80% sequence identity to the above amino acids, specifically at least 90%, more specifically at least 95%, and even more specifically at least 99%, may be included as long as they exhibit the activities of the wild-type SerA or SerA variants where the feedback inhibition on serine is released, but are not limited thereto. The variants where the feedback inhibition is released represent those proteins in which a modification is introduced on the SerA-encoding gene by insertion, substitution, etc., thereby enabling maintaining of the activity from the feedback inhibition by serine or glycine, or having enhanced activities thereof, and those variants where the feedback inhibition is released are already well known (Grant G A et al., J. Biol. Chem., 39: 5357-5361, 1999; Grant G A et al., Biochem., 39: 7316-7319, 2000; Grant G A et al., J. Biol. Chem., 276: 17844-17850, 2001; Peters-Wendisch P et al., Appl. Microbiol. Biotechnol., 60: 437-441, 2002; EP Pat. No. EP0943687B).

Additionally, the polynucleotide sequence encoding the wild-type SerA or the variants where the feedback inhibition on serine is released may be a polynucleotide sequence encoding any one amino acid sequence represented by SEQ ID NO: 18 or SEQ ID NO: 19, but is not limited thereto. Due to the genetic code degeneracy or considering the codons preferred by organisms to express the polypeptide, various modifications on the polynucleotide may be executed on the coding region within the scope not changing the amino acid sequence of the polypeptide. The polynucleotide sequence may be, for example, any one of polynucleotide sequences represented by SEQ ID NO: 20 or SEQ ID NO: 25, and may have a nucleotide sequence having a homology to the polynucleotide sequences of at least 80%, and specifically at least 90%, but is not limited thereto.

The SerC may be a protein having an amino acid sequence which is, for example, represented by SEQ ID NO: 21, but is not limited thereto. Additionally, the amino acid sequence, as long as it exhibits the activity of SerC, may also include amino acid sequences which have a sequence identity to the above amino acid sequence of at least 80%, specifically at least 90%, more specifically at least 95%, and even more specifically at least 99%, but is not limited thereto.

Additionally, the polynucleotide sequence encoding the SerC may be the polynucleotide sequence encoding the amino acid represented by SEQ ID NO: 21. Due to the genetic code degeneracy or considering the codons preferred by organisms to express the polypeptide, various modifications on the polynucleotide may be executed on the coding region within the scope not changing the amino acid sequence of the polypeptide. The polynucleotide sequence may be, for example, one represented by SEQ ID NO: 22, and may have a nucleotide sequence having a homology to the polynucleotide sequence of at least 80%, and specifically at least 90%, but is not limited thereto.

As used herein, the term "endogenous activity" refers to an active state of a polypeptide in a microorganism in a wild-type state or a state before modification. As used herein, the term "enhancement compared to its endogenous activity" refers to an increased activity of a polypeptide in a microorganism compared with that possessed in its wild-type state or a pre-modification state, and is a concept including rendering the activity of a particular polypeptide in a microorganism which does not possess the activity of the particular polypeptide.

As used herein, the term "enhancement of activity" refers to, although it is not particularly limited to, not only the drawing of a higher effect than the original function due to the increase in the activity of a polypeptide itself, but also the increase in its activity due to the increase in enzyme activity by the increase of endogenous gene activity, endogenous gene amplification by the internal or external factors, replacement, modification, or mutation of a promoter, etc. Specifically, the enhancement of activity may be performed by methods such as a method for increasing copy number of a gene encoding the polypeptide in a cell, a method for modifying the regulation sequence of a gene encoding the polypeptide, a method for substituting the gene encoding the polypeptide on the chromosome with a mutated gene to increase the activity of the polypeptide, a method for introducing a modification in the gene encoding the polypeptide on the chromosome to enhance the activity of the polypeptide, etc., but the methods are not limited thereto. These methods for enhancing activity may be referenced in the same manner to enhance the activities of other polypeptides of the present disclosure.

Specifically, the enhancement of activity in the present disclosure may be achieved by at least one method selected from the group consisting of a method for increasing copy number of a gene encoding the SerA or SerC in a cell; a method for introducing a modification in the regulation sequence of a gene encoding the SerA or SerC on the chromosome; a method for substituting the regulation sequence of a gene encoding the SerA or SerC on the chromosome with a sequence having strong activity; a method for substituting a gene encoding the SerA or SerC on the chromosome with a mutated gene to increase the activity of the SerA or SerC; and a method of introducing a modification in a gene encoding the SerA or SerC on the chromosome to enhance the activity of the SerA or SerC.

In the above, the increase in gene copy number, although not particularly limited thereto, may be performed in a state operably connected to a vector, or by being inserted into the chromosome within a host cell. Specifically, the method may be executed by introducing a vector, to which a polynucleotide encoding the protein of the present disclosure is operably connected, and which can be replicated and function irrespective of a host, into a cell of the host; or introducing a vector, to which the polynucleotide is operably connected, capable of inserting the polynucleotide into the chromosome of the host cell, into the host cell. The insertion of the polynucleotide into the chromosome may be performed using a known method in the art, for example, by homologous recombination.

Then, the modification of the expression regulation sequence for increasing the expression of a polynucleotide, although not particularly limited thereto, may be performed by inducing a modification in the polynucleotide sequence via deletion, insertion, conservative substitution, non-conservative substitution, or a combination thereof so as to further enhance the activity of the expression regulation sequence; or by replacing the polynucleotide sequence with a nucleic acid sequence with a stronger activity. The expression regulation sequence, although not particularly limited thereto, may include a promoter, an operator sequence, a sequence encoding a ribosome-binding domain, and a sequence for regulating termination of transcription and translation, etc.

A strong promoter, instead of the original promoter, may be connected to the upper end of the expression unit of the polynucleotide, but is not limited thereto. Examples of the known strong promoters may include cjl promoter (Korean Patent No. 10-0620092), lac promoter, trp promoter, trc promoter, tac promoter, lambda phage PR promoter, PL promoter, and tet promoter, but are not limited thereto Additionally, the modification of the polynucleotide sequence on the chromosome, although not particularly limited thereto, may be performed by inducing a modification on the expression regulation sequence of the polynucleotide sequence via deletion, insertion, conservative substitution, non-conservative substitution, or a combination thereof so as to further enhance the activity of the polynucleotide sequence; or by replacing the polynucleotide sequence with an enhanced polynucleotide sequence having a stronger activity.

Generally, the introduction and enhancement of the protein activity may increase the activity or concentration of the corresponding protein relative to the activity or concentration of a wild-type protein or in a microorganism strain at the initial stage from at least 1%, 10%, 25%, 50%, 75%, 100%, 150%, 200%, 300%, 400%, or 500%, to a maximum of 1000% or 2000%, but is not limited thereto.

Additionally, the microorganism may be a microorganism which is further weakened in its capability to introduce the OPS into a cell or decompose. Specifically, the activities of PhnC/PhnD/PhnE alkylphosphonate ABC transporter (PhnCDE operon, specifically an ATP-binding component of phosphonate transporter (PhnC; EG 10713)-periplasmic binding protein component of Pn transporter (PhnD; EG 10714)-integral membrane component of the alkylphosphonate ABC transporter (PhnE; EG 11283)), alkaline phosphatase (PhoA), or acid phosphatase (AphA) may be weakened compared with their endogenous activities.

Additionally, the microorganism of the present disclosure may be further enhanced with the activity of nucleotide transhydrogenase (PntAB; EC 1.6.1.1). The PntAB, as specified in the earlier reference (Sauer U P et al., J Biol Chem. 20; 279(8): 6613-9. Epub 2003), is involved in the metabolism of NADPH and controls the intracellular redox balance.

Regarding the contents of the OPS-producing microorganism, the disclosures in Korean Patent No. 1381048 or US Patent Application Publication No. 2012-0190081 may be used as references of the present disclosure, in addition to those described above.

In still another aspect, the present disclosure provides a method for producing OPS, comprising culturing the OPS-producing microorganism expresses the polypeptide having OPS-exporting activity, i.e., a YhhS MFS transporter polypeptide variant, in a medium.

In the present disclosure, the OPS, the polypeptide having OPS-exporting activity, YhhS MFS transporter, and the OPS-producing microorganism are the same as explained above.

Specifically, the method may include culturing the OPS-producing microorganism expresses a polypeptide represented by an amino acid sequence selected from the group consisting of SEQ ID NO: 1, SEQ ID NO: 3, and SEQ ID NO: 5; and separating OPS from the OPS-producing microorganism or the medium in the above step, but the method is not limited thereto.

As used herein, the term "culturing" refers to growing the microorganism in an appropriately adjusted environment. The culture process may be performed according to the appropriate medium and conditions for culture known in the art. The culture process may be easily adjusted for use by a skilled person in the art according to the strain to be selected. Specifically, the culture may be a batch culture, a continuous culture, and a fetch culture, but is not limited thereto.

In culturing the recombinant microorganism having reduced SerB activity compared to its endogenous activity, the medium may further contain glycine or serine, because the serine requirement of the recombinant microorganism is induced. Glycine may be provided in the form of purified glycine, a glycine-containing yeast extract, or tryptone. The concentration of glycine to be contained in the medium is generally 0.1 g/L to 10 g/L, and specifically 0.5 g/L to 3 g/L. Additionally, serine may be provided in the form of purified serine, a serine-containing yeast extract, or tryptone. The concentration of serine to be contained in the medium is generally 0.1 g/L to 5 g/L, and specifically 0.1 g/L to 1 g/L.

Examples of the carbon source to be contained in the medium may include saccharides and carbohydrates such as glucose, sucrose, lactose, fructose, maltose, starch, and cellulose; oils and fats such as soybean oil, sunflower oil, castor oil, and coconut oil; fatty acids such as palmitic acid, stearic acid, and linoleic acid; alcohols such as glycerol and ethanol; and organic acids such as acetic acid. These carbon sources may be used alone or in combination, but are not limited thereto. Examples of the nitrogen source to be contained in the medium may include organic nitrogen sources such as peptone, yeast extract, meat gravy, malt extract, corn steep liquor, and bean flour; and inorganic nitrogen sources such as urea, ammonium sulfate, ammonium chloride, ammonium phosphate, ammonium carbonate, and ammonium nitrate. These nitrogen sources may be used alone or in combination, but are not limited thereto. As a phosphorous source, the culture media may further contain potassium dihydrogen phosphate, dipotassium hydrogen phosphate, and corresponding sodium-containing salts, but is not limited thereto. The culture media may include metals such as magnesium sulfate and iron sulfate. Additionally, amino acids, vitamins and appropriate precursors may be contained. These culture media or precursors may be added to the culture in the form of a batch culture or continuous culture, but are not limited thereto.

Additionally, the pH of the culture may be adjusted by adding a compound such as ammonium hydroxide, potassium hydroxide, ammonia, phosphoric acid, and sulfuric acid during cultivation in an appropriate manner. Additionally, bubble formation may be prevented during the cultivation using an antifoaming agent such as fatty acid polyglycol ester. Additionally, oxygen gas or a gas containing oxygen may be added to a culture in order to maintain aerobic conditions in a culture liquid; or nitrogen gas, hydrogen gas, or carbon dioxide may be injected to maintain anaerobic or microaerobic conditions. The culture temperature may be in the range from 27° C. to 37° C., and specifically from 30° C. to 35° C. The cultivation may be continued until the production of a desired material can be obtained, and specifically for from 10 hours to 100 hours, but is not limited to these illustrative examples.

In the present disclosure, the OPS produced during the cultivation may be further separated and purified. The intended OPS may be recovered from the culture using an appropriate method known in the art, according to the culture method, e.g., a batch culture, a continuous culture, and a fetch culture, but is not limited thereto.

In still another aspect, the present disclosure provides a method for producing cysteine or a derivative thereof, which includes culturing the OPS-producing microorganism expresses the polypeptide having OPS-exporting activity, i.e., a YhhS MFS transporter polypeptide variant, in a medium to producing O-phosphoserine; and reacting the OPS produced above with a sulfide, in the presence of O-phosphoserine sulfhydrylase(OPSS) or a microorganism expressing the OPSS.

Additionally, the present disclosure provides a method for producing cysteine or a derivative thereof, which includes culturing an OPS-producing microorganism expresses the polypeptide having OP S-exporting activity, i.e., a YhhS MFS transporter polypeptide variant, in a medium to producing O-phosphoserine; separating OPS from the OPS-producing microorganism or the medium in the above step; and reacting the OPS produced above with a sulfide, in the presence of OPSS or a microorganism expressing the OPSS.

In the present disclosure, OPS, a polypeptide having the OPS-exporting activity, YhhS MFS transporters, and an OPS-producing microorganism are the same as described above.

As used herein, the term "O-phosphoserine sulfhydrylase (OPSS)" refers to a polypeptide that catalyzes a reaction in which a thiol (SH) group is provided to OPS to convert OPS into cysteine. The enzyme was first found in *Aeropyrum pernix, Mycobacterium tuberculosis, Mycobacterium smegmatics*, and *Trichomonas vaginalis* (Mino K and Ishikawa K, FEBS Letters, 551: 133-138, 2003; Burns K E et al., J. Am. Chem. Soc., 127: 11602-11603, 2005). Additionally, the scope of OPSS includes not only wild-type OPSS protein, but also variants that include deletion, substitution, or addition in part of the polynucleotide sequence encoding the OPSS which show activity that is equal to or higher than the biological activity of wild-type OPSS protein, and also includes all the OPSS proteins disclosed in Korean Patent Nos. 1381048 and 1208267 and their variants.

The sulfide to be used in the present disclosure may be any sulfide provided not only in a solid form generally used in the art, but also in a liquid or gas form due to the difference in pH, pressure, and solubility, and thus can be converted to a thiol (SH) group in the form of, for example, sulfide ($S^{2-}$) or thiosulfate ($S_2O_3^{2-}$). Specifically, the sulfide to be used in the present disclosure may include $Na_2S$, NaSH, $H_2S$, $(NH_4)_2S$, and $Na_2S_2O_3$, which can provide a thiol group to OPS, but is not limited thereto. In the reaction, a single thiol group is provided to a single reactive OPS group to produce a single cysteine or a derivative thereof. In this reaction, a sulfide is specifically added in an amount of 0.1 to 3 molar equivalents, and specifically 1 to 2 molar equivalents based on the molar concentration of OPS, but is not limited thereto. The economically optimal conversion may occur when OPS and the sulfide providing thiol groups are provided in a 1:1 (one to one) molar ratio.

In addition, the method of the present disclosure may further include separating and purifying the cysteine produced in the above reaction step. In particular, the desired cysteine may be recovered by separation and purification from the reaction solution using a suitable reaction known in the art.

Additionally, the cysteine prepared according to the method of the present disclosure may be easily synthesized by a chemical synthesis reaction known in the art.

As used herein, the term "derivatives" refers to similar compounds obtained by chemically modifying a portion of any compound. Usually, the term refers to compounds in which a hydrogen atom or a particular atom group is substituted with another hydrogen atom or atom group.

As used herein, the term "cysteine derivatives" refers to compounds in which a hydrogen atom or a particular atom group in cysteine is substituted with another atom or atom group. For example, the cysteine derivatives may have a form in which the nitrogen atom of the amine group (—NH₂) or the sulfur atom of the thiol group (—SH) in cysteine has another atom or atom group attached thereto. Examples of cysteine derivatives may include N-acetylcysteine (NAC), S-carboxymethylcysteine (SCMC), Boc-Cys (Me)-OH, (R)—S-(2-amino-2-carboxyethyl)-L-homocysteine, (R)-2-amino-3-sulfopropionic acid, D-2-amino-4-(ethylthio)butyric acid, 3-sulfino-L-alanine, Fmoc-Cys(Boc-methyl)-OH, seleno-L-cysteine, S-(2-thiazolyl)-L-cysteine, S-(2-thienyl)-L-cysteine, S-(4-tolyl)-L-cysteine, but are not limited thereto. Cysteine can easily be synthesized into N-acetylcysteine (NAC) by a reaction with an acetylation agent, and in basic conditions, it can be synthesized into S-carboxymethylcysteine (SCMC) by a reaction with a haloacetic acid. These cysteine derivatives are used mainly as pharmaceutical materials for antitussive agents, cough-relieving agents, and therapeutic agents for bronchitis, bronchial asthma, laryngopharyngitis, etc.

In still another aspect, the present disclosure provides a use of exporting OPS by the polypeptide which is represented by an amino acid sequence selected from the group consisting of SEQ ID NO: 1, SEQ ID NO: 3, and SEQ ID NO: 5.

MODE FOR INVENTION

Hereinafter, the present disclosure will be described in more detail with reference to the following Examples. However, these Examples are for illustrative purposes only, and the disclosure is not intended to be limited by these Examples.

Example 1

Preparation of YhhS Major Facilitator Superfamily (MFS) Transporter Variants

In order to improve the activity of the OPS exporter for the improvement of OPS-exporting activity in an OPS-producing strain, variants were prepared for the YhhS major facilitator superfamily (MFS) transporter (SEQ ID NO: 23), a newly identified OPS-exporter protein, and yhhS (SEQ ID NO: 24), a gene encoding the same. The detailed process is described herein below.

First, a library of yhhS gene variants was constructed. To this end, a random mutagenesis PCR (JENA error-prone PCR) was performed using a gene-specific primer pair (SEQ ID NOS: 7 and 8) based on the genomic DNA of *Escherichia coli* K12_W3110 (ATCC27325) as a template. The thus-prepared gene fragments from the mutagenesis were cloned into a pCLPrhtB vector, wherein rhtB promoter (SEQ ID NO: 13), which was subjected to PCR using a gene-specific primer pair (SEQ ID NOS: 14 and 15), was inserted into the SacI-EcoRV site of a pCL1920 vector (GenBank No AB236930). Specifically, the pCLPrhtB vector was cut with EcoRV and PstI, and then the gene fragments from the mutagenesis were cloned thereinto using In-fusion Cloning Kit (Clontech Laboratories, Inc.). The cloning was performed at 50° C. for 10 minutes, thereby completing the construction of plasmid libraries of pCL PrhtB yhhS variants.

The thus-constructed recombinant plasmid libraries were screened via high throughput screening (HTS). In particular, the platform strain used for screening was CA07-0012 (KCCM11121P), which is a recombinant microorganism modified to reduce the activity of endogenous phosphoserine phosphatase (SerB) in the wild-type *E. coli* strain W3110 (Korean Patent No. 10-1381048; US Patent Application Publication No. 2012-0190081).

Subsequently, in order to obtain variants with improved OPS-exporting activity, the thus-constructed plasmid libraries were transformed into the platform strain CA07-0012 via electroporation, cultured in media containing an excess amount of OPS, and three colonies where the growth inhibition was released were selected. Then, plasmids were obtained from the three selected colonies and analyzed via sequencing technology.

As such, three yhhS variants which are involved in the removal of growth inhibition under the OPS-added condition were selected, and these were named as yhhS M2, yhhS M25, and yhhS M45, respectively.

Upon analysis of the nucleotide sequences of the yhhS M2, yhhS M25, and yhhS M45, it was confirmed that yhhS M2 has the amino acid sequence represented by SEQ ID NO: 1, yhhS M25 has that represented by SEQ ID NO: 3, and yhhS M45 has that represented by SEQ ID NO: 5.

Example 2

Confirmation of OPS-Exporting Activity by YhhS Variants in OPS-Producing Strain 2-1. Construction of a Strain with Enhanced YhhS MFS Transporter Using CA07-0012 and Evaluation of OPS-Producing Capability The plasmids containing the three different variants identified in Example 1 were respectively transformed into CA07-0012, the OPS-producing strain, by an electric-pulse method conventionally used in the art. As such, OPS-producing strains introduced with the yhhS variants, i.e., CA07-0012/pCL-PrhtB-yhhS M2, CA07-0012/pCL-PrhtB-yhhS M25, and CA07-0012/pCL-PrhtB-yhhS M45, were constructed, and these were named as *Escherichia coli* CA07-0345, *Escherichia coli* CA07-0344, and *Escherichia coli* CA07-0346, respectively. Additionally, the *Escherichia coli* CA07-0344, *Escherichia coli* CA07-0345, and *Escherichia coli* CA07-0346 strains were deposited with the Korean Culture Center of Microorganisms (KCCM), recognized as an international depositary authority under the Budapest Treaty, on Jul. 23, 2015, under the Accession Numbers of KCCM11736P, KCCM11737P, and KCCM11738P, respectively.

The OPS-producing capabilities of the corresponding strains were evaluated.

Specifically, each strain was plated out on a solid LB medium and cultured in a 33° C. incubator overnight. The strains cultured in the solid LB medium overnight were inoculated into a 25 mL titer medium shown in Table 1 below and cultured in a 34.5° C. incubator at a rate of 200 rpm for 48 hours. The results are shown in Table 2 below.

TABLE 1

| Composition | Conc. (per 1 L) |
| --- | --- |
| Glucose | 50 g |
| KH₂PO₄ | 6 g |
| (NH₄)₂SO₄ | 17 g |
| MgSO₄•7H₂O | 1 g |
| FeSO₄•7H₂O | 5 mg |
| MnSO₄•4H₂O | 10 mg |
| L-Glycine | 2.5 g |
| Yeast extract | 3 g |
| Calcium carbonate | 30 g |
| pH | 6.8 |

TABLE 2

| Strain | OD 562 nm | Glucose consumption (g/L) | O-Phosphoserine (g/L) |
|---|---|---|---|
| CA07-0012/pCL-PrhtB-yhhS (wt) | 23.9 | 40.5 | 1.38 |
| CA07-0345 (CA07-0012/pCL-PrhtB-yhhS M2) | 29.4 | 42.8 | 1.78 |
| CA07-0344 (CA07-0012/pCL-PrhtB-yhhS M25) | 32.7 | 44.3 | 2.28 |
| CA07-0346 (CA07-0012/pCL-PrhtB-yhhS M45) | 27.0 | 42.8 | 2.16 |

As shown in Table 2 above, in the case of strains introduced with yhhS variants of the present disclosure, these showed an excellent result demonstrating an increase of OPS production by from 128% to 165%, compared to the strain introduced with a wild-type yhhS gene. Specifically, the yhhS M2 variant showed a 128% increase, the yhhS M25 variant showed a 165% increase, and the yhhS M45 variant showed a 156% increase compared to that of the wild-type, respectively.

2-2. Construction of a Strain with Enhanced YhhS MFS Transporter Using Strains with Enhanced SerA and SerC and Evaluation of OPS-Producing Capability In order to reconfirm the activity of yhhS variants of the present disclosure, CA07-0022/pCL-Prmf-serA*(G336V)-serC (KCCM11103P, Korean Patent No. 10-1381048), which, being an OPS-producing strain with improved OPS-producing capability, has enhanced activity of D-3-phosphoglycerate dehydrogenase (SerA) and 3-phosphoserine aminotransferase (SerC) as OPS biosynthesis pathways, was used.

For the construction of a pCL-Prmf-serA(G336V)-serC PrhtB-genes vector, each of the yhhS variants was amplified using a primer pair (SEQ ID NOS: 9 and 10) based on the pCL-PrhtB-yhhS variant as a template, and the resultants were cloned into the HindIII restriction site of the pCL-Prmf-serA*(G336V)-serC vector.

Specifically, the strains, where each of the plasmids was transformed by the conventionally used electric-pulse method, were plated out on a solid LB medium and then cultured in a 33° C. incubator overnight. The strains cultured in the solid LB medium overnight were inoculated into a 25 mL titer medium shown in Table 1 above and cultured in a 34.5° C. incubator at a rate of 200 rpm for 48 hours. The results are shown in Table 3 below.

TABLE 3

| Strain | OD 562 nm | Glucose consumption (g/L) | O-Phosphoserine (g/L) |
|---|---|---|---|
| CA07-0022/pCL-Prmf-serA*(G336V)-(RBS)serC-PrhtB-yhhS(wt) | 28.9 | 40.5 | 3.79 |
| CA07-0022/pCL-Prmf-serA*(G336V)-(RBS)serC-PrhtB-yhhS M2 | 28.2 | 42.8 | 4.96 |
| CA07-0022/pCL-Prmf-serA*(G336V)-(RBS)serC-PrhtB-yhhS M25 | 32.2 | 44.3 | 6.68 |
| CA07-0022/pCL-Prmf-serA*(G336V)-(RBS)serC-PrhtB-yhhS M45 | 30.7 | 42.8 | 5.01 |

As shown in Table 3 above, it was confirmed that when the yhhS variants of the present disclosure were introduced to an OPS-producing strain with an enhanced OPS biosynthesis gene, the OPS production was increased by from 130% to 176%. These results indicate that the yhhS variants of the present disclosure can be effectively used for OPS production.

2-3. Construction of a Strain with Enhanced YhhS MFS Transporter According to Promoter Strength on the Chromosome and Evaluation of OPS-Producing Capability Further to the above experiments, in order to confirm whether the OPS-exporting activity is improved when the yhhS variants are introduced on the chromosome, the self-promoter of the microorganism was substituted with the pCJ1 promoter (Korean Patent No. 10-0620092), and the strains introduced with the variants of the present disclosure were constructed and their OPS-producing capability evaluated. The introduction of the pCJ1 promoter and the variants into the chromosome was performed by the methods conventionally used in the art. First, for transformation, a recombinant vector was inserted into CA07-0022/pCL-Prmf-serA*(G336V)-serC (KCCM11103P, Korean Patent No. 10-1381048), the OPS-producing strain, by an electric-pulse method (Appl Microbiol Biotechnol. 1999 October; 52(4):541-5) as the primary step. Then, the strains inserted into the chromosome by recombination of homologous sequences were selected in a medium containing 25 mg/L kanamycin. The thus-selected primary strains were subjected to the secondary step of cross-over, and then the strains where the pCJ1 promoter and the variants were substituted and the vector was removed were selected.

Finally, the presence of substitution of the promoter and the variants of the transformed strains were confirmed by performing a PCR using the primer pair (SEQ ID NOS: 11 and 12).

Each of the strains was plated out on a solid LB medium and then cultured in a 33° C. incubator overnight. The strains cultured in the LB solid medium overnight were inoculated into a 25 mL titer medium shown in Table 1 above and cultured in a 34.5° C. incubator at a rate of 200 rpm for 40 hours. The results are shown in Table 4 below.

TABLE 4

| Strain | OD 562 nm | Glucose consumption (g/L) | O-Phosphoserine (g/L) |
|---|---|---|---|
| CA07-0022/pCL-Prmf-serA*(G336V)-serC | 30.0 | 37.1 | 1.7 |
| CA07-0022::Pcj1 yhhS (WT)/pCL-Prmf-serA*(G336V)-serC | 30.2 | 40.1 | 2.2 |
| CA07-0022::Pcj1 yhhS M2/pCL-Prmf-serA*(G336V)-serC | 39.9 | 43.2 | 2.9 |
| CA07-0022::Pcj1 yhhS M25/pCL-Prmf-serA*(G336V)-serC | 35.3 | 44.1 | 3.8 |
| CA07-0022::Pcj1 yhhS M45/pCL-Prmf-serA*(G336V)-serC | 42.0 | 43.5 | 3.2 |

As shown in Table 4 above, it was confirmed that when the activity of each protein variant was increased on the chromosome, the amount of OPS production by the protein variant showed a maximum of 172% compared to that of the strain introduced with the wild-type yhhS.

From the foregoing, a skilled person in the art to which the present disclosure pertains will be able to understand that the present disclosure may be embodied in other specific forms without modifying the technical concepts or essential characteristics of the present disclosure. In this regard, the exemplary embodiments disclosed herein are only for illustrative purposes and should not be construed as limiting the scope of the present disclosure. On the contrary, the present disclosure is intended to cover not only the exemplary embodiments but also various alternatives, modifications, equivalents, and other embodiments that may be included within the spirit and scope of the present disclosure as defined by the appended claims.

The invention claimed is:

1. A polypeptide having O-phosphoserine (OPS) exporting activity, comprising an amino acid sequence selected from the group consisting of SEQ ID NO: 1, SEQ ID NO: 3, and SEQ ID NO: 5.

2. A polynucleotide encoding the polypeptide of claim 1.

3. The polynucleotide according to claim 2, wherein the polynucleotide comprises a nucleotide sequence selected from the group consisting of SEQ ID NO: 2, SEQ ID NO: 4, and SEQ ID NO: 6.

4. A microorganism of the genus *Escherichia* producing O-phosphoserine, wherein the microorganism expresses the polypeptide of claim 1.

5. The microorganism according to claim 4, wherein an activity of phosphoserine phosphatase (SerB) is further weakened compared to its endogenous activity.

6. The microorganism according to claim 4, wherein an activity of phosphoglycerate dehydrogenase (SerA) or phosphoserine aminotransferase (SerC) is further enhanced compared to its endogenous activity.

7. The microorganism according to claim 4, wherein the microorganism of the genus *Escherichia* is *Escherichia coli*.

8. A method for producing O-phosphoserine (OPS) comprising culturing the microorganism of claim 4 in a medium.

9. A method for producing cysteine or a derivative thereof, comprising:
   culturing the microorganism of claim 4 in a medium to produce O-phosphoserine (OPS); and
   reacting said O-phosphoserine with a sulfide, in the presence of O-phosphoserine sulfhydrylase (OPSS) or a microorganism expressing the same.

10. The method according to claim 9, wherein the sulfide is at least one selected from the group consisting of $Na_2S$, $NaSH$, $(NH_4)_2S$, $H_2S$, and $Na_2S_2O_3$.

* * * * *

SEQUENCE LISTING

<160> NUMBER OF SEQ ID NOS: 25

<210> SEQ ID NO 1
<211> LENGTH: 405
<212> TYPE: PRT
<213> ORGANISM: Artificial Sequence
<220> FEATURE:
<223> OTHER INFORMATION: Escherichia coli K12 W3110 YhhS MFS
      transporter, YhhS M2

<400> SEQUENCE: 1

```
Met Pro Glu Pro Val Ala Glu Pro Ala Leu Asn Gly Leu Arg Leu Asn
1               5                   10                  15

Leu Arg Ile Val Ser Ile Val Met Phe Asn Phe Ala Ser Tyr Leu Thr
            20                  25                  30

Ile Gly Leu Pro Leu Ala Val Leu Pro Gly Tyr Val His Asp Val Val
        35                  40                  45

Gly Phe Ser Ala Phe Trp Ala Gly Leu Val Ile Ser Leu Gln Tyr Phe
    50                  55                  60

Ala Thr Leu Leu Ser Arg Pro His Ala Gly Arg Tyr Ala Asp Ser Leu
65                  70                  75                  80

Gly Pro Lys Lys Ile Val Phe Gly Leu Cys Gly Cys Phe Leu Ser
                85                  90                  95

Gly Leu Gly Tyr Leu Thr Ala Gly Leu Thr Ala Ser Leu Pro Val Ile
                100                 105                 110

Ser Leu Leu Leu Cys Leu Gly Arg Val Ile Leu Gly Ile Gly Gln
            115                 120                 125

Ser Phe Ala Gly Thr Gly Ser Thr Leu Trp Gly Val Gly Val Val Gly
    130                 135                 140

Ser Leu His Ile Gly Arg Val Ile Ser Trp Asn Gly Ile Val Thr Tyr
145                 150                 155                 160

Gly Ala Met Ala Met Gly Ala Pro Leu Gly Val Val Phe Tyr His Trp
                165                 170                 175

Gly Gly Leu Gln Ala Leu Ala Leu Ile Ile Met Gly Val Ala Leu Val
            180                 185                 190

Ala Ile Leu Leu Ala Ile Pro Arg Pro Thr Val Lys Ala Ser Lys Gly
        195                 200                 205

Lys Pro Leu Pro Phe Arg Ala Val Leu Gly Arg Val Trp Leu Tyr Gly
    210                 215                 220

Met Ala Leu Ala Leu Ala Ser Ala Gly Phe Gly Val Ile Ala Thr Phe
225                 230                 235                 240

Ile Thr Leu Phe Tyr Asp Ala Lys Gly Trp Asp Gly Ala Ala Phe Ala
                245                 250                 255

Leu Thr Leu Phe Ser Cys Ala Phe Val Gly Thr Arg Leu Leu Phe Pro
            260                 265                 270

Asn Gly Ile Asn Arg Ile Gly Gly Leu Asn Val Ala Met Ile Cys Phe
        275                 280                 285

Ser Val Glu Ile Ile Gly Leu Leu Leu Val Gly Val Ala Thr Met Pro
    290                 295                 300

Trp Met Ala Lys Ile Gly Val Leu Leu Ala Gly Ala Gly Phe Ser Leu
305                 310                 315                 320

Val Phe Pro Ala Leu Gly Val Val Ala Ile Lys Ala Val Pro Gln Gln
                325                 330                 335

Asn Gln Gly Ala Ala Leu Ala Thr Tyr Thr Val Phe Met Asp Leu Ser
            340                 345                 350
```

Leu Gly Val Thr Gly Pro Leu Ala Gly Leu Val Met Ser Trp Ala Gly
        355                 360                 365

Val Pro Val Ile Tyr Leu Ala Ala Ala Gly Leu Val Ala Ile Ala Leu
    370                 375                 380

Leu Leu Thr Trp Arg Leu Lys Lys Arg Pro Pro Glu His Val Pro Glu
385                 390                 395                 400

Ala Ala Ser Ser Ser
            405

<210> SEQ ID NO 2
<211> LENGTH: 1218
<212> TYPE: DNA
<213> ORGANISM: Artificial Sequence
<220> FEATURE:
<223> OTHER INFORMATION: Escherichia coli K12 W3110 YhhS MFS
      transporter, YhhS M2

<400> SEQUENCE: 2

| | | |
|---|---|---|
| atgcccgaac cgtagccga acccgcgcta acggattgc gcctgaattt gcgcattgtc | 60 |
| tctatagtca tgtttaactt cgccagctac ctcaccatcg ggttgccgct cgctgtatta | 120 |
| ccgggctatg tccatgatgt ggtgggcttt agcgccttct gggcaggatt ggttatcagc | 180 |
| ctgcaatatt tcgccaccct gctgagccgc cctcatgccg acgttacgc cgattcgctg | 240 |
| ggacccaaaa agattgtcgt cttcggttta tgcggctgct ttttgagcgg tctgggtat | 300 |
| ctgacggcag gattaaccgc cagtctgcct gtcatcagcc tgttattact ttgcctgggg | 360 |
| cgcgtcatcc ttgggattgg gcaaagtttt gccggaacgg gatcgaccct atggggcgtt | 420 |
| ggcgtggttg gctcgctgca tatcgggcgg gtgatttcgt ggaacggcat tgtcacttac | 480 |
| ggggcgatgg cgatgggtgc gccgttaggc gtcgtgtttt atcactgggg cggcttgcag | 540 |
| gcgttagcgt taatcattat gggcgtggcg ctggtggcca ttttgttggc gatcccgcgt | 600 |
| ccgacggtaa aagccagtaa aggcaaaccg ctgccgtttc gcgcggtgct gggcgcgtc | 660 |
| tggctgtacg gtatggcgct ggcactggct tccgccggat ttggcgtcat cgccaccttt | 720 |
| atcacgctgt tttatgacgc taaaggttgg gacggtgcgg ctttcgcgct gacgctgttt | 780 |
| agctgtgcgt ttgtcggtac gcgtttgtta ttccctaacg gcattaaccg tatcggtggc | 840 |
| ttaaacgtag cgatgatttg ctttagcgtt gagataatcg gcctgctact ggttggcgtg | 900 |
| gcgactatgc cgtggatggc gaaaatcggc gtcttactgg cggggccgg gttttcgctg | 960 |
| gtgttcccgg cattgggtgt agtggcgata aaagcggttc gcagcaaaa tcaggggcg | 1020 |
| gcgctggcaa cttacaccgt atttatggat ttatcgcttg gcgtgactgg accactggct | 1080 |
| gggctggtga tgagctgggc gggcgtaccg gtgatttatc tggcggcggc gggactggtc | 1140 |
| gcaatcgcgt tattactgac gtggcgatta aaaaaacggc ctccggaaca cgtccctgag | 1200 |
| gccgcctcat catcttaa | 1218 |

<210> SEQ ID NO 3
<211> LENGTH: 405
<212> TYPE: PRT
<213> ORGANISM: Artificial Sequence
<220> FEATURE:
<223> OTHER INFORMATION: Escherichia coli K12 W3110 YhhS MFS
      transporter, YhhS M25

<400> SEQUENCE: 3

Met Pro Glu Pro Val Ala Glu Pro Ala Leu Asn Gly Leu Arg Leu Asn
1               5                   10                  15

Leu Arg Ile Val Ser Ile Val Met Phe Asn Phe Ala Ser Tyr Leu Thr
                 20                  25                  30

Ile Gly Leu Pro Leu Ala Val Leu Pro Gly Tyr Val His Asp Val Met
             35                  40                  45

Gly Phe Ser Ala Phe Trp Ala Gly Leu Val Ile Ser Leu Gln Tyr Phe
 50                  55                  60

Ala Thr Leu Leu Ser Arg Pro His Ala Gly Arg Tyr Ala Asp Ser Leu
 65                  70                  75                  80

Gly Pro Lys Lys Ile Val Val Phe Gly Leu Cys Gly Cys Phe Leu Ser
                 85                  90                  95

Gly Leu Gly Tyr Leu Thr Ala Gly Leu Thr Ala Ser Leu Pro Val Ile
                100                 105                 110

Ser Leu Leu Leu Cys Leu Gly Arg Val Ile Leu Gly Ile Gly Gln
                115                 120                 125

Ser Phe Ala Gly Thr Gly Ser Thr Leu Trp Gly Val Gly Val Val Gly
            130                 135                 140

Ser Leu His Ile Gly Arg Val Ile Ser Trp Asn Gly Ile Val Thr Tyr
145                 150                 155                 160

Gly Ala Met Ala Met Gly Ala Pro Leu Gly Val Val Ser Tyr His Trp
                165                 170                 175

Gly Gly Leu Gln Ala Leu Ala Leu Ile Ile Met Gly Val Ala Leu Val
            180                 185                 190

Ala Ile Leu Leu Ala Ile Pro Arg Pro Thr Val Lys Ala Ser Lys Gly
        195                 200                 205

Lys Pro Leu Pro Phe Arg Ala Val Leu Gly Arg Val Trp Leu Tyr Gly
    210                 215                 220

Met Ala Leu Ala Leu Ala Ser Ala Gly Phe Gly Val Ile Ala Ser Phe
225                 230                 235                 240

Ile Thr Leu Phe Tyr Asp Ala Lys Gly Trp Asp Gly Ala Ala Phe Ala
                245                 250                 255

Leu Thr Leu Phe Ser Cys Ala Phe Val Gly Thr Arg Leu Leu Phe Pro
            260                 265                 270

Asn Gly Ile Asn Arg Ile Gly Gly Leu Asn Val Ala Met Ile Cys Phe
        275                 280                 285

Ser Val Glu Ile Ile Gly Leu Leu Val Gly Val Ala Thr Met Pro
    290                 295                 300

Trp Met Ala Lys Ile Gly Val Leu Leu Ala Gly Ala Gly Phe Ser Leu
305                 310                 315                 320

Val Phe Pro Ala Leu Gly Val Val Ala Ile Lys Ala Ile Pro Gln Gln
                325                 330                 335

Asn Gln Gly Ala Ala Leu Ala Thr Tyr Thr Val Phe Met Asp Leu Ser
            340                 345                 350

Leu Gly Val Thr Gly Pro Leu Ala Gly Leu Val Met Ser Trp Ala Gly
        355                 360                 365

Val Pro Val Ile Tyr Leu Ala Ala Gly Leu Val Ala Ile Ala Leu
    370                 375                 380

Leu Leu Thr Trp Arg Leu Lys Lys Arg Pro Pro Glu His Val Pro Glu
385                 390                 395                 400

Ala Ala Ser Ser Ser
                405

<210> SEQ ID NO 4
<211> LENGTH: 1218
<212> TYPE: DNA

<213> ORGANISM: Artificial Sequence
<220> FEATURE:
<223> OTHER INFORMATION: Escherichia coli K12 W3110 YhhS MFS
      transporter, YhhS M25

<400> SEQUENCE: 4

```
atgcccgaac cgtagccga acccgcgcta acggattgc gcctgaattt gcgcattgtc    60
tctatagtca tgtttaactt cgccagctac ctcaccatcg ggttgccgct cgctgtatta   120
ccgggctatg tccatgatgt gatgggcttt agcgccttct gggcaggatt ggttatcagc   180
ctgcaatatt tcgccacctt gctgagccgc cctcatgccg acgttacgc cgattcgctg    240
ggacccaaaa agattgtcgt cttcggttta tgcggctgct ttttgagcgg tctgggtat    300
ctgacggcag gattaaccgc cagtctgcct gtcatcagcc tgttattact ttgcctgggg   360
cgcgtcatcc ttgggattgg gcaaagtttt gccggaacgg gatcgaccct atggggcgtt   420
ggcgtggttg gctcgctgca tatcgggcgg gtgatttcgt ggaacggcat tgtcacttac   480
ggggcgatgg cgatgggtgc gccgttaggc gtcgtgtctt atcactgggg cggcttgcag   540
gcgttagcgt taatcattat gggcgtggcg ctggtggcca ttttgttggc gatcccgcgt   600
ccgacggtaa aagccagtaa aggcaaaccg ctgccgtttc gcgcggtgct ggggcgcgtc   660
tggctgtacg gtatggcgct ggcactggcc tccgccggat ttggcgtcat cgcctccttt   720
atcacgctgt tttatgacgc taaaggttgg gacggtgcgg cttcgcgct gacgctgttt    780
agctgtgcgt ttgtcggtac gcgtttgtta ttccctaacg gcattaaccg tatcggtggc   840
ttaaacgtag cgatgatttg ctttagcgtt gagataatcg gcctgctact ggttggcgtg   900
gcgactatgc cgtggatggc gaaaatcggc gtcttactgg cggggccgg gttttcgctg    960
gtgttcccgg cattgggtgt agtggcgata aaagcgattc cgcagcaaaa tcaggggcg   1020
gcgctggcaa cttacaccgt atttatggat ttatcgcttg gcgtgactgg accactggct   1080
gggctggtga tgagctgggc gggcgtaccg gtgatttatc tggcggcggc gggactggtc   1140
gcaatcgcgt tattactgac gtggcgatta aaaaaacggc ctccggaaca cgtccctgag   1200
gccgcctcat catcttaa                                                 1218
```

<210> SEQ ID NO 5
<211> LENGTH: 405
<212> TYPE: PRT
<213> ORGANISM: Artificial Sequence
<220> FEATURE:
<223> OTHER INFORMATION: Escherichia coli K12 W3110 YhhS MFS
      transporter, YhhS M45

<400> SEQUENCE: 5

```
Met Pro Glu Pro Val Ala Glu Pro Ala Leu Asn Gly Leu Arg Leu Asn
1               5                   10                  15

Leu Arg Ile Val Ser Ile Val Met Phe Asn Phe Ala Ser Tyr Leu Thr
            20                  25                  30

Ile Gly Leu Pro Leu Ala Val Leu Pro Gly Tyr Val His Asp Val Met
        35                  40                  45

Gly Phe Ser Ala Phe Trp Ala Gly Leu Val Ile Ser Leu Gln Tyr Phe
    50                  55                  60

Ala Thr Leu Leu Ser Arg Pro His Ala Gly Arg Tyr Ala Asp Ser Leu
65                  70                  75                  80

Gly Pro Lys Lys Ile Val Val Leu Gly Leu Cys Gly Cys Phe Leu Ser
                85                  90                  95

Gly Leu Gly Tyr Leu Thr Ala Gly Leu Thr Ala Ser Leu Pro Val Ile
```

100                 105                 110
Ser Leu Leu Leu Leu Cys Leu Gly Arg Val Ile Leu Gly Ile Gly Gln
            115                 120                 125

Ser Phe Ala Gly Thr Gly Ser Thr Leu Trp Gly Val Gly Val Val Gly
        130                 135                 140

Ser Leu His Ile Gly Arg Val Ile Ser Trp Asn Gly Ile Val Thr Tyr
145                 150                 155                 160

Gly Ala Met Ala Met Gly Ala Pro Leu Gly Val Val Phe Tyr His Trp
                165                 170                 175

Gly Gly Leu Gln Ala Leu Ala Leu Ile Ile Met Gly Val Ala Leu Val
            180                 185                 190

Ala Ile Leu Leu Ala Ile Pro Arg Pro Thr Val Lys Ala Ser Arg Gly
            195                 200                 205

Lys Pro Leu Pro Phe Arg Ala Val Leu Gly Arg Val Trp Leu Tyr Gly
        210                 215                 220

Met Ala Leu Ala Leu Ala Ser Ala Gly Phe Gly Val Ile Ala Thr Phe
225                 230                 235                 240

Thr Thr Leu Phe Tyr Val Ala Lys Gly Trp Asp Gly Ala Ala Phe Ala
                245                 250                 255

Leu Thr Leu Phe Ser Cys Ala Phe Val Gly Thr Arg Leu Leu Phe Pro
            260                 265                 270

Asn Gly Ile Asn Arg Ile Gly Gly Leu Asn Val Ala Met Ile Cys Phe
        275                 280                 285

Ser Val Glu Ile Ile Gly Leu Leu Leu Val Gly Val Ala Thr Met Pro
    290                 295                 300

Trp Met Ala Lys Ile Gly Val Leu Leu Ala Gly Ala Gly Phe Ser Leu
305                 310                 315                 320

Val Phe Pro Ala Leu Gly Val Val Ala Ile Lys Ala Val Pro Gln Gln
                325                 330                 335

Asn Gln Gly Ala Ala Leu Ala Thr Tyr Thr Val Phe Met Asp Leu Ser
            340                 345                 350

Leu Gly Val Thr Gly Pro Leu Ala Gly Leu Val Met Ser Trp Ala Gly
        355                 360                 365

Val Pro Val Ile Tyr Leu Ala Ala Gly Leu Val Ala Ile Ala Leu
        370                 375                 380

Leu Leu Thr Trp Arg Leu Lys Lys Arg Pro Pro Glu His Val Pro Glu
385                 390                 395                 400

Ala Ala Ser Ser Ser
            405

<210> SEQ ID NO 6
<211> LENGTH: 1218
<212> TYPE: DNA
<213> ORGANISM: Artificial Sequence
<220> FEATURE:
<223> OTHER INFORMATION: Escherichia coli K12 W3110 YhhS MFS
      transporter, YhhS M45

<400> SEQUENCE: 6
atgcccgaac cgtagccga acccgcgcta acggattgc gcctgaattt gcgcattgtc     60
tctatagtca tgtttaactt cgccagctac ctcaccatcg ggttgccgct cgctgtatta    120
ccgggctatg tccatgatgt gatgggcttt agcgccttct gggcaggatt ggttatcagc    180
ctgcaatatt tcgccaccct gctgagccgc cctcatgccg acgttacgc cgattcgctg    240 ggacccaaaa agattgtcgt cctcggttta tgcggctgct ttttgagcgg cctgggggtat    300

```
ctgacggcag gattaaccgc cagtctgcct gtcatcagcc tgttattact ttgcctgggg      360
cgcgtcatcc ttgggattgg gcaaagtttt gccggaacgg gatcgaccct atggggcgtt      420
ggcgtggttg gctcgctgca tatcgggcgg gtgatttcgt ggaacggcat tgtcacttac      480
ggggcgatgg cgatgggtgc gccgttaggc gtcgtgtttt atcactgggg cggcttgcag      540
gcgttagcgt taatcattat gggcgtggcg ctggtggcca ttttgttggc gatcccgcgt      600
ccgacggtaa aagccagtag aggcaaaccg ctgccgtttc gcgcggtgct gggcgcgtc       660 tggctgtacg gtatggcgct ggcactggct tccgccggat ttggcgtcat cgccaccttt      720
accacgctgt tttatgtcgc taaaggttgg gacggtgcgg cttcgcgcgct gacgctgttt     780 agctgtgcgt ttgtcggtac gcgtttgtta ttccctaacg gcattaaccg tatcggtggc      840
ttaaacgtag cgatgatttg ctttagcgtt gagataatcg gcctgctact ggttggcgtg      900
gcgactatgc cgtggatggc gaaaatcggc gtcttactgg cggggccggg gttttcgctg      960
gtgttcccgg cattgggtgt agtggcgata aaagcggttc cgcagcaaaa tcaggggggcg    1020 gcgctggcaa cttacaccgt atttatggat ttatcgcttg gcgtgactgg accactggct    1080
gggctggtga tgagctgggc gggcgtaccg gtgatttatc tggcggcggc gggactggtc    1140
gcaatcgcgt tattactgac gtggcgatta aaaaaacggc ctccggaaca cgtccctgag    1200
gccgcctcat catcttaa                                                  1218

<210> SEQ ID NO 7
<211> LENGTH: 30
<212> TYPE: DNA
<213> ORGANISM: Artificial Sequence
<220> FEATURE:
<223> OTHER INFORMATION: primer for amplification of yhhS  to construct
      pCL-PrhtB-yhhS library

<400> SEQUENCE: 7
tctgcctctt aaaccatgcc cgaacccgta                                       30

<210> SEQ ID NO 8
<211> LENGTH: 30
<212> TYPE: DNA
<213> ORGANISM: Artificial Sequence
<220> FEATURE:
<223> OTHER INFORMATION: primer for amplification of yhhS  to construct
      pCL-PrhtB-yhhS library

<400> SEQUENCE: 8
cttgcatgcc tgcagttaag atgatgaggc                                       30

<210> SEQ ID NO 9
<211> LENGTH: 27
<212> TYPE: DNA
<213> ORGANISM: Artificial Sequence
<220> FEATURE:
<223> OTHER INFORMATION: primer for amplification of pCL-PrhtB-genes to
      constrct pCL-Prmf-serA(G336V)-serC_PrhtB-genes

<400> SEQUENCE: 9
aagcttcggg cctcttcgct attacgc                                          27

<210> SEQ ID NO 10
<211> LENGTH: 27
<212> TYPE: DNA
<213> ORGANISM: Artificial Sequence
<220> FEATURE:
<223> OTHER INFORMATION: primer for amplification of pCL-PrhtB-genes to
``` constrct pCL-Prmf-serA(G336V)-serC_PrhtB-genes

<400> SEQUENCE: 10
aagcttaggc ttacccgtct tactgtc                                          27

<210> SEQ ID NO 11
<211> LENGTH: 21
<212> TYPE: DNA
<213> ORGANISM: Artificial Sequence
<220> FEATURE:
<223> OTHER INFORMATION: primer for confirm of chromosome changed yhhS

<400> SEQUENCE: 11
gagtagcgtc ttcaatgcaa g                                                21

<210> SEQ ID NO 12
<211> LENGTH: 19
<212> TYPE: DNA
<213> ORGANISM: Artificial Sequence
<220> FEATURE:
<223> OTHER INFORMATION: primer for confirm of chromosome changed yhhS

<400> SEQUENCE: 12
gcgttagtgt ctttatcat                                                   19

<210> SEQ ID NO 13
<211> LENGTH: 200
<212> TYPE: DNA
<213> ORGANISM: Escherichia coli

<400> SEQUENCE: 13
agatgactac cacccggtca tggtgctgtg cgcgaaaacg dacaaagcgc accggaatgt       60
catccacacc agtaaactct gcttcatcac gctgacgcca gaaatcagtc agcggtccca      120
tggtaaaagc agcaaacgcg tttttctcttg tttcccagtc ttttttgctgc tgaaacatcg    180 ggtaatctgc ctcttaaacc                                                  200

<210> SEQ ID NO 14
<211> LENGTH: 29
<212> TYPE: DNA
<213> ORGANISM: Artificial Sequence
<220> FEATURE:
<223> OTHER INFORMATION: primer for amplification of PrhtB to construct
      pCL-PrhtB vector

<400> SEQUENCE: 14
gatcgagctc agatgactac cacccggtc                                        29

<210> SEQ ID NO 15
<211> LENGTH: 35
<212> TYPE: DNA
<213> ORGANISM: Artificial Sequence
<220> FEATURE:
<223> OTHER INFORMATION: primer for amplification of PrhtB to construct
      pCL-PrhtB vector

<400> SEQUENCE: 15
gatcgagctc gatatcgatg aactcccggt gtgtc                                 35

<210> SEQ ID NO 16
<211> LENGTH: 322
<212> TYPE: PRT
<213> ORGANISM: Escherichia coli

<400> SEQUENCE: 16

```
Met Pro Asn Ile Thr Trp Cys Asp Leu Pro Glu Asp Val Ser Leu Trp
1               5                   10                  15

Pro Gly Leu Pro Leu Ser Leu Ser Gly Asp Glu Val Met Pro Leu Asp
            20                  25                  30

Tyr His Ala Gly Arg Ser Gly Trp Leu Leu Tyr Gly Arg Gly Leu Asp
        35                  40                  45

Lys Gln Arg Leu Thr Gln Tyr Gln Ser Lys Leu Gly Ala Ala Met Val
    50                  55                  60

Ile Val Ala Ala Trp Cys Val Glu Asp Tyr Gln Val Ile Arg Leu Ala
65              70                  75                  80

Gly Ser Leu Thr Ala Arg Ala Thr Arg Leu Ala His Glu Ala Gln Leu
                85                  90                  95

Asp Val Ala Pro Leu Gly Lys Ile Pro His Leu Arg Thr Pro Gly Leu
            100                 105                 110

Leu Val Met Asp Met Asp Ser Thr Ala Ile Gln Ile Glu Cys Ile Asp
            115                 120                 125

Glu Ile Ala Lys Leu Ala Gly Thr Gly Glu Met Val Ala Glu Val Thr
130                 135                 140

Glu Arg Ala Met Arg Gly Glu Leu Asp Phe Thr Ala Ser Leu Arg Ser
145                 150                 155                 160

Arg Val Ala Thr Leu Lys Gly Ala Asp Ala Asn Ile Leu Gln Gln Val
                165                 170                 175

Arg Glu Asn Leu Pro Leu Met Pro Gly Leu Thr Gln Leu Val Leu Lys
                180                 185                 190

Leu Glu Thr Leu Gly Trp Lys Val Ala Ile Ala Ser Gly Gly Phe Thr
            195                 200                 205

Phe Phe Ala Glu Tyr Leu Arg Asp Lys Leu Arg Leu Thr Ala Val Val
    210                 215                 220

Ala Asn Glu Leu Glu Ile Met Asp Gly Lys Phe Thr Gly Asn Val Ile
225                 230                 235                 240

Gly Asp Ile Val Asp Ala Gln Tyr Lys Ala Lys Thr Leu Thr Arg Leu
                245                 250                 255

Ala Gln Glu Tyr Glu Ile Pro Leu Ala Gln Thr Val Ala Ile Gly Asp
            260                 265                 270

Gly Ala Asn Asp Leu Pro Met Ile Lys Ala Ala Gly Leu Gly Ile Ala
            275                 280                 285

Tyr His Ala Lys Pro Lys Val Asn Glu Lys Ala Glu Val Thr Ile Arg
        290                 295                 300

His Ala Asp Leu Met Gly Val Phe Cys Ile Leu Ser Gly Ser Leu Asn
305                 310                 315                 320

Gln Lys

<210> SEQ ID NO 17
<211> LENGTH: 969
<212> TYPE: DNA
<213> ORGANISM: Escherichia coli

<400> SEQUENCE: 17
atgcctaaca ttacctggtg cgacctgcct gaagatgtct ctttatggcc gggtctgcct      60
ctttcattaa gtggtgatga agtgatgcca ctggattacc acgcaggtcg tagcggctgg     120
ctgctgtatg gtcgtgggct ggataaacaa cgtctgaccc aataccagag caaactgggt     180
gcggcgatgg tgattgttgc cgcctggtgc gtggaagatt atcaggtgat tcgtctggca     240
```

```
ggttcactca ccgcacgggc tacacgcctg gcccacgaag cgcagctgga tgtcgccccg    300
ctggggaaaa tcccgcacct gcgcacgccg ggtttgctgg tgatggatat ggactccacc    360
gccatccaga ttgaatgtat tgatgaaatt gccaaactgg ccggaacggg cgagatggtg    420
gcggaagtaa ccgaacgggc gatgcgcggc gaactcgatt ttaccgccag cctgcgcagc    480
cgtgtggcga cgctgaaagg cgctgacgcc aatattctgc aacaggtgcg tgaaaatctg    540
ccgctgatgc caggcttaac gcaactggtg ctcaagctgg aaacgctggg ctggaaagtg    600
gcgattgcct ccggcggctt tactttcttt gctgaatacc tgcgcgacaa gctgcgcctg    660
accgccgtgg tagccaatga actggagatc atggacggta aatttaccgg caatgtgatc    720
ggcgacatcg tagacgcgca gtacaaagcg aaaactctga ctcgcctcgc gcaggagtat    780
gaaatcccgc tggcgcagac cgtggcgatt ggcgatggag ccaatgacct gccgatgatc    840
aaagcggcag ggctggggat tgcctaccat gccaagccaa aagtgaatga aaaggcggaa    900
gtcaccatcc gtcacgctga cctgatgggg gtattctgca tcctctcagg cagcctgaat    960
cagaagtaa                                                             969
```

```
<210> SEQ ID NO 18
<211> LENGTH: 410
<212> TYPE: PRT
<213> ORGANISM: Escherichia coli

<400> SEQUENCE: 18

Met Ala Lys Val Ser Leu Glu Lys Asp Lys Ile Lys Phe Leu Leu Val
1               5                   10                  15

Glu Gly Val His Gln Lys Ala Leu Glu Ser Leu Arg Ala Ala Gly Tyr
            20                  25                  30

Thr Asn Ile Glu Phe His Lys Gly Ala Leu Asp Asp Glu Gln Leu Lys
        35                  40                  45

Glu Ser Ile Arg Asp Ala His Phe Ile Gly Leu Arg Ser Arg Thr His
    50                  55                  60

Leu Thr Glu Asp Val Ile Asn Ala Ala Glu Lys Leu Val Ala Ile Gly
65                  70                  75                  80

Cys Phe Cys Ile Gly Thr Asn Gln Val Asp Leu Asp Ala Ala Lys
                85                  90                  95

Arg Gly Ile Pro Val Phe Asn Ala Pro Phe Ser Asn Thr Arg Ser Val
            100                 105                 110

Ala Glu Leu Val Ile Gly Glu Leu Leu Leu Leu Arg Gly Val Pro
        115                 120                 125

Glu Ala Asn Ala Lys Ala His Arg Gly Val Trp Asn Lys Leu Ala Ala
    130                 135                 140

Gly Ser Phe Glu Ala Arg Gly Lys Lys Leu Gly Ile Ile Gly Tyr Gly
145                 150                 155                 160

His Ile Gly Thr Gln Leu Gly Ile Leu Ala Glu Ser Leu Gly Met Tyr
                165                 170                 175

Val Tyr Phe Tyr Asp Ile Glu Asn Lys Leu Pro Leu Gly Asn Ala Thr
            180                 185                 190

Gln Val Gln His Leu Ser Asp Leu Leu Asn Met Ser Asp Val Val Ser
        195                 200                 205

Leu His Val Pro Glu Asn Pro Ser Thr Lys Asn Met Met Gly Ala Lys
    210                 215                 220

Glu Ile Ser Leu Met Lys Pro Gly Ser Leu Leu Ile Asn Ala Ser Arg
225                 230                 235                 240
```

```
Gly Thr Val Val Asp Ile Pro Ala Leu Cys Asp Ala Leu Ala Ser Lys
            245                 250                 255

His Leu Ala Gly Ala Ala Ile Asp Val Phe Pro Thr Glu Pro Ala Thr
        260                 265                 270

Asn Ser Asp Pro Phe Thr Ser Pro Leu Cys Glu Phe Asp Asn Val Leu
        275                 280                 285

Leu Thr Pro His Ile Gly Gly Ser Thr Gln Glu Ala Gln Glu Asn Ile
    290                 295                 300

Gly Leu Glu Val Ala Gly Lys Leu Ile Lys Tyr Ser Asp Asn Gly Ser
305                 310                 315                 320

Thr Leu Ser Ala Val Asn Phe Pro Glu Val Ser Leu Pro Leu His Gly
                325                 330                 335

Gly Arg Arg Leu Met His Ile His Glu Asn Arg Pro Gly Val Leu Thr
            340                 345                 350

Ala Leu Asn Lys Ile Phe Ala Glu Gln Gly Val Asn Ile Ala Ala Gln
        355                 360                 365

Tyr Leu Gln Thr Ser Ala Gln Met Gly Tyr Val Ile Asp Ile Glu
    370                 375                 380

Ala Asp Glu Asp Val Ala Glu Lys Ala Leu Gln Ala Met Lys Ala Ile
385                 390                 395                 400

Pro Gly Thr Ile Arg Ala Arg Leu Leu Tyr
                405                 410

<210> SEQ ID NO 19
<211> LENGTH: 410
<212> TYPE: PRT
<213> ORGANISM: Artificial Sequence
<220> FEATURE:
<223> OTHER INFORMATION: Escherichia coli K12 W3110 serA MT

<400> SEQUENCE: 19

Met Ala Lys Val Ser Leu Glu Lys Asp Lys Ile Lys Phe Leu Leu Val
1               5                   10                  15

Glu Gly Val His Gln Lys Ala Leu Glu Ser Leu Arg Ala Ala Gly Tyr
            20                  25                  30

Thr Asn Ile Glu Phe His Lys Gly Ala Leu Asp Asp Glu Gln Leu Lys
        35                  40                  45

Glu Ser Ile Arg Asp Ala His Phe Ile Gly Leu Arg Ser Arg Thr His
    50                  55                  60

Leu Thr Glu Asp Val Ile Asn Ala Ala Glu Lys Leu Val Ala Ile Gly
65                  70                  75                  80

Cys Phe Cys Ile Gly Thr Asn Gln Val Asp Leu Asp Ala Ala Ala Lys
                85                  90                  95

Arg Gly Ile Pro Val Phe Asn Ala Pro Phe Ser Asn Thr Arg Ser Val
            100                 105                 110

Ala Glu Leu Val Ile Gly Glu Leu Leu Leu Leu Leu Arg Gly Val Pro
        115                 120                 125

Glu Ala Asn Ala Lys Ala His Arg Gly Val Trp Asn Lys Leu Ala Ala
    130                 135                 140

Gly Ser Phe Glu Ala Arg Gly Lys Lys Leu Gly Ile Ile Gly Tyr Gly
145                 150                 155                 160

His Ile Gly Thr Gln Leu Gly Ile Leu Ala Glu Ser Leu Gly Met Tyr
                165                 170                 175

Val Tyr Phe Tyr Asp Ile Glu Asn Lys Leu Pro Leu Gly Asn Ala Thr
            180                 185                 190
```

```
Gln Val Gln His Leu Ser Asp Leu Leu Asn Met Ser Asp Val Val Ser
            195                 200                 205

Leu His Val Pro Glu Asn Pro Ser Thr Lys Asn Met Met Gly Ala Lys
    210                 215                 220

Glu Ile Ser Leu Met Lys Pro Gly Ser Leu Leu Ile Asn Ala Ser Arg
225                 230                 235                 240

Gly Thr Val Val Asp Ile Pro Ala Leu Cys Asp Ala Leu Ala Ser Lys
                245                 250                 255

His Leu Ala Gly Ala Ala Ile Asp Val Phe Pro Thr Glu Pro Ala Thr
            260                 265                 270

Asn Ser Asp Pro Phe Thr Ser Pro Leu Cys Glu Phe Asp Asn Val Leu
        275                 280                 285

Leu Thr Pro His Ile Gly Gly Ser Thr Gln Glu Ala Gln Glu Asn Ile
    290                 295                 300

Gly Leu Glu Val Ala Gly Lys Leu Ile Lys Tyr Ser Asp Asn Gly Ser
305                 310                 315                 320

Thr Leu Ser Ala Val Asn Phe Pro Glu Val Ser Leu Pro Leu His Val
                325                 330                 335

Gly Arg Arg Leu Met His Ile His Glu Asn Arg Pro Gly Val Leu Thr
            340                 345                 350

Ala Leu Asn Lys Ile Phe Ala Glu Gln Gly Val Asn Ile Ala Ala Gln
        355                 360                 365

Tyr Leu Gln Thr Ser Ala Gln Met Gly Tyr Val Val Ile Asp Ile Glu
    370                 375                 380

Ala Asp Glu Asp Val Ala Glu Lys Ala Leu Gln Ala Met Lys Ala Ile
385                 390                 395                 400

Pro Gly Thr Ile Arg Ala Arg Leu Leu Tyr
                405                 410

<210> SEQ ID NO 20
<211> LENGTH: 1233
<212> TYPE: DNA
<213> ORGANISM: Escherichia coli

<400> SEQUENCE: 20
atggcaaagg tatcgctgga gaaagacaag attaagtttc tgctggtaga aggcgtgcac      60
caaaaggcgc tggaaagcct tcgtgcagct ggttacacca acatcgaatt tcacaaaggc     120
gcgctggatg atgaacaatt aaaagaatcc atccgcgatg cccacttcat cggcctgcga     180
tcccgtaccc atctgactga agacgtgatc aacgccgcag aaaaactggt cgctattggc     240
tgtttctgta tcggaacaaa ccaggttgat ctggatgcgg cggcaaagcg cgggatcccg     300
gtatttaacg caccgttctc aaatacgcgc tctgttgcgg agctggtgat ggcgaactg      360 ctgctgctat tgcgcggcgt gccggaagcc aatgctaaag cgcaccgtgg cgtgtggaac     420
aaactggcgg cggttctttt tgaagcgcgc ggcaaaaagc tgggtatcat cggctacggt     480
catattggta cgcaattggg cattctggct gaatcgctgg aatgtatgt ttactttat      540 gatattgaaa ataaactgcc gctgggcaac gccactcagg tacagcatct ttctgacctg     600
ctgaatatga gcgatgtggt gagtctgcat gtaccagaga atccgtccac caaaaatatg     660
atgggcgcga agaaatttc actaatgaag cccggctcgc tgctgattaa tgcttcgcgc     720
ggtactgtgg tggatattcc ggcgctgtgt gatgcgctgg cgagcaaaca tctggcgggg     780
gcggcaatcg acgtattccc gacgaaccg gcgaccaata gcgatccatt tacctctccg     840
ctgtgtgaat tcgacaacgt ccttctgacg ccacacattg gcggttcgac tcaggaagcg     900
```

```
caggagaata tcggcctgga agttgcgggt aaattgatca agtattctga caatggctca    960
acgctctctg cggtgaactt cccggaagtc tcgctgccac tgcacggtgg gcgtcgtctg   1020
atgcacatcc acgaaaaccg tccgggcgtg ctaactgcgc tgaacaaaat cttcgccgag   1080
cagggcgtca acatcgccgc gcaatatctg caaacttccg cccagatggg ttatgtggtt   1140
attgatattg aagccgacga agacgttgcc gaaaaagcgc tgcaggcaat gaaagctatt   1200
ccgggtacca ttcgcgcccg tctgctgtac taa                                1233
```

<210> SEQ ID NO 21
<211> LENGTH: 362
<212> TYPE: PRT
<213> ORGANISM: Escherichia coli

<400> SEQUENCE: 21

```
Met Ala Gln Ile Phe Asn Phe Ser Ser Gly Pro Ala Met Leu Pro Ala
1               5                   10                  15

Glu Val Leu Lys Gln Ala Gln Gln Glu Leu Arg Asp Trp Asn Gly Leu
            20                  25                  30

Gly Thr Ser Val Met Glu Val Ser His Arg Gly Lys Glu Phe Ile Gln
        35                  40                  45

Val Ala Glu Glu Ala Glu Lys Asp Phe Arg Asp Leu Leu Asn Val Pro
    50                  55                  60

Ser Asn Tyr Lys Val Leu Phe Cys His Gly Gly Arg Gly Gln Phe
65                  70                  75                  80

Ala Ala Val Pro Leu Asn Ile Leu Gly Asp Lys Thr Thr Ala Asp Tyr
                85                  90                  95

Val Asp Ala Gly Tyr Trp Ala Ala Ser Ala Ile Lys Glu Ala Lys Lys
            100                 105                 110

Tyr Cys Thr Pro Asn Val Phe Asp Ala Lys Val Thr Val Asp Gly Leu
        115                 120                 125

Arg Ala Val Lys Pro Met Arg Glu Trp Gln Leu Ser Asp Asn Ala Ala
    130                 135                 140

Tyr Met His Tyr Cys Pro Asn Glu Thr Ile Asp Gly Ile Ala Ile Asp
145                 150                 155                 160

Glu Thr Pro Asp Phe Gly Ala Asp Val Val Val Ala Ala Asp Phe Ser
                165                 170                 175

Ser Thr Ile Leu Ser Arg Pro Ile Asp Val Ser Arg Tyr Gly Val Ile
            180                 185                 190

Tyr Ala Gly Ala Gln Lys Asn Ile Gly Pro Ala Gly Leu Thr Ile Val
        195                 200                 205

Ile Val Arg Glu Asp Leu Leu Gly Lys Ala Asn Ile Ala Cys Pro Ser
    210                 215                 220

Ile Leu Asp Tyr Ser Ile Leu Asn Asp Asn Gly Ser Met Phe Asn Thr
225                 230                 235                 240

Pro Pro Thr Phe Ala Trp Tyr Leu Ser Gly Leu Val Phe Lys Trp Leu
                245                 250                 255

Lys Ala Asn Gly Gly Val Ala Glu Met Asp Lys Ile Asn Gln Gln Lys
            260                 265                 270

Ala Glu Leu Leu Tyr Gly Val Ile Asp Asn Ser Asp Phe Tyr Arg Asn
        275                 280                 285

Asp Val Ala Lys Ala Asn Arg Ser Arg Met Asn Val Pro Phe Gln Leu
    290                 295                 300

Ala Asp Ser Ala Leu Asp Lys Leu Phe Leu Glu Glu Ser Phe Ala Ala
```

Gly Leu His Ala Leu Lys Gly His Arg Val Val Gly Met Arg Ala
305                 310                 315                 320

Ser Ile Tyr Asn Ala Met Pro Leu Glu Gly Val Lys Ala Leu Thr Asp
              325                 330                 335

Phe Met Val Glu Phe Glu Arg Arg His Gly
              340                 345                 350

355                 360

<210> SEQ ID NO 22
<211> LENGTH: 1089
<212> TYPE: DNA
<213> ORGANISM: Escherichia coli

<400> SEQUENCE: 22
atggctcaaa tcttcaattt tagttctggt ccggcaatgc taccggcaga ggtgcttaaa      60
caggctcaac aggaactgcg cgactggaac ggtcttggta cgtcggtgat ggaagtgagt     120
caccgtggca agagttcat tcaggttgca gaggaagccg agaaggattt tcgcgatctt      180
cttaatgtcc cctccaacta caaggtatta ttctgccatg gcggtggtcg cggtcagttt     240
gctgcggtac cgctgaatat tctcggtgat aaaaccaccg cagattatgt tgatgccggt     300
tactgggcgg caagtgccat taagaagcg aaaaaatact gcacgcctaa tgtctttgac      360
gccaaagtga ctgttgatgg tctgcgcgcg gttaagccaa tgcgtgaatg caactctct     420
gataatgctg cttatatgca ttattgcccg aatgaaacca tcgatggtat cgccatcgac     480
gaaacgccag acttcggcgc agatgtggtg gtcgccgctg acttctcttc aaccattctt     540
tcccgtccga ttgacgtcag ccgttatggt gtaatttacg ctggcgcgca gaaaaatatc     600
ggcccggctg gcctgacaat cgtcatcgtt cgtgaagatt tgctgggcaa agcgaatatc     660
gcgtgtccgt cgattctgga ttattccatc ctcaacgata acggctccat gtttaacacg     720
ccgccgacat ttgcctggta tctatctggt ctggtctttta aatggctgaa agcgaacggc     780
ggtgtagctg aaatggataa aatcaatcag caaaaagcag aactgctata tggggtgatt     840
gataacagcg atttctaccg caatgacgtg gcgaaagcta accgttcgcg gatgaacgtg     900
ccgttccagt tggcggacag tgcgcttgac aaattgttcc ttgaagagtc ttttgctgct     960
ggccttcatg cactgaaagg tcaccgtgtg gtcggcggaa tgcgcgcttc tatttataac    1020
gccatgccgc tggaaggcgt taaagcgctg acagacttca tggttgagtt cgaacgccgt    1080
cacggttaa                                                            1089

<210> SEQ ID NO 23
<211> LENGTH: 405
<212> TYPE: PRT
<213> ORGANISM: Escherichia coli

<400> SEQUENCE: 23

Met Pro Glu Pro Val Ala Glu Pro Ala Leu Asn Gly Leu Arg Leu Asn
1               5                   10                  15

Leu Arg Ile Val Ser Ile Val Met Phe Asn Phe Ala Ser Tyr Leu Thr
              20                  25                  30

Ile Gly Leu Pro Leu Ala Val Leu Pro Gly Tyr Val His Asp Val Met
          35                  40                  45

Gly Phe Ser Ala Phe Trp Ala Gly Leu Val Ile Ser Leu Gln Tyr Phe
      50                  55                  60

Ala Thr Leu Leu Ser Arg Pro His Ala Gly Arg Tyr Ala Asp Ser Leu
65                  70                  75                  80

Gly Pro Lys Lys Ile Val Val Phe Gly Leu Cys Gly Cys Phe Leu Ser
                85                  90                  95

Gly Leu Gly Tyr Leu Thr Ala Gly Leu Thr Ala Ser Leu Pro Val Ile
            100                 105                 110

Ser Leu Leu Leu Leu Cys Leu Gly Arg Val Ile Leu Gly Ile Gly Gln
        115                 120                 125

Ser Phe Ala Gly Thr Gly Ser Thr Leu Trp Gly Val Gly Val Val Gly
    130                 135                 140

Ser Leu His Ile Gly Arg Val Ile Ser Trp Asn Gly Ile Val Thr Tyr
145                 150                 155                 160

Gly Ala Met Ala Met Gly Ala Pro Leu Gly Val Val Phe Tyr His Trp
                165                 170                 175

Gly Gly Leu Gln Ala Leu Ala Leu Ile Ile Met Gly Val Ala Leu Val
            180                 185                 190

Ala Ile Leu Leu Ala Ile Pro Arg Pro Thr Val Lys Ala Ser Lys Gly
        195                 200                 205

Lys Pro Leu Pro Phe Arg Ala Val Leu Gly Arg Val Trp Leu Tyr Gly
    210                 215                 220

Met Ala Leu Ala Leu Ala Ser Ala Gly Phe Gly Val Ile Ala Thr Phe
225                 230                 235                 240

Ile Thr Leu Phe Tyr Asp Ala Lys Gly Trp Asp Gly Ala Ala Phe Ala
                245                 250                 255

Leu Thr Leu Phe Ser Cys Ala Phe Val Gly Thr Arg Leu Leu Phe Pro
            260                 265                 270

Asn Gly Ile Asn Arg Ile Gly Gly Leu Asn Val Ala Met Ile Cys Phe
        275                 280                 285

Ser Val Glu Ile Ile Gly Leu Leu Leu Val Gly Val Ala Thr Met Pro
    290                 295                 300

Trp Met Ala Lys Ile Gly Val Leu Leu Ala Gly Ala Gly Phe Ser Leu
305                 310                 315                 320

Val Phe Pro Ala Leu Gly Val Val Ala Val Lys Ala Val Pro Gln Gln
                325                 330                 335

Asn Gln Gly Ala Ala Leu Ala Thr Tyr Thr Val Phe Met Asp Leu Ser
            340                 345                 350

Leu Gly Val Thr Gly Pro Leu Ala Gly Leu Val Met Ser Trp Ala Gly
        355                 360                 365

Val Pro Val Ile Tyr Leu Ala Ala Gly Leu Val Ala Ile Ala Leu
    370                 375                 380

Leu Leu Thr Trp Arg Leu Lys Lys Arg Pro Pro Glu His Val Pro Glu
385                 390                 395                 400

Ala Ala Ser Ser Ser
            405

<210> SEQ ID NO 24
<211> LENGTH: 1218
<212> TYPE: DNA
<213> ORGANISM: Escherichia coli

<400> SEQUENCE: 24
atgcccgaac ccgtagccga acccgcgcta acggattgc gcctgaattt gcgcattgtc      60
tctatagtca tgtttaactt cgccagctac ctcaccatcg ggttgccgct cgctgtatta     120
ccgggctatg tccatgatgt gatgggcttt agcgccttct gggcaggatt ggttatcagc     180
ctgcaatatt tcgccaccct gctgagccgc cctcatgccg acgttacgc cgattcgctg      240

```
ggacccaaaa agattgtcgt cttcggttta tgcggctgct ttttgagcgg tctggggtat        300
ctgacggcag gattaaccgc cagtctgcct gtcatcagcc tgttattact ttgcctgggg        360
cgcgtcatcc ttgggattgg gcaaagtttt gccggaacgg gatcgaccct atggggcgtt        420
ggcgtggttg gctcgctgca tatcgggcgg gtgatttcgt ggaacggcat tgtcacttac        480
ggggcgatgg cgatgggtgc gccgttaggc gtcgtgtttt atcactgggg cggcttgcag        540
gcgttagcgt taatcattat gggcgtggcg ctggtggcca ttttgttggc gatcccgcgt        600
ccgacggtaa aagccagtaa aggcaaaccg ctgccgtttc gcgcggtgct gggcgcgtc         660 tggctgtacg gtatggcgct ggcactggct tccgccggat ttggcgtcat cgccaccttt       720
atcacgctgt tttatgacgc taaaggttgg gacggtgcgg ctttcgcgct gacgctgttt       780
agctgtgcgt tgtcggtac gcgtttgtta ttccctaacg gcattaaccg tatcggtggc        840
ttaaacgtag cgatgatttg ctttagcgtt gagataatcg gcctgctact ggttggcgtg       900
gcgactatgc cgtggatggc gaaaatcggc gtcttactgg cggggccgg gttttcgctg        960 gtgttcccgg cattgggtgt agtggcggta aaagcggttc cgcagcaaaa tcaggggcg       1020 gcgctggcaa cttacaccgt atttatggat ttatcgcttg gcgtgactgg accactggct      1080
gggctggtga tgagctgggc gggcgtaccg gtgatttatc tggcggcggc gggactggtc      1140
gcaatcgcgt tattactgac gtggcgatta aaaaaacggc ctccggaaca cgtccctgag      1200
gccgcctcat catcttaa                                                   1218
```

<210> SEQ ID NO 25
<211> LENGTH: 1233
<212> TYPE: DNA
<213> ORGANISM: Artificial Sequence
<220> FEATURE:
<223> OTHER INFORMATION: Escherichia coli K12 W3110 serA MT

<400> SEQUENCE: 25

```
atggcaaagg tatcgctgga gaaagacaag attaagtttc tgctggtaga aggcgtgcac         60
caaaaggcgc tggaaagcct tcgtgcagct ggttacacca acatcgaatt tcacaaaggc        120
gcgctggatg atgaacaatt aaaagaatcc atccgcgatg cccacttcat cggcctgcga        180
tcccgtaccc atctgactga agacgtgatc aacgccgcag aaaaactggt cgctattggc        240
tgtttctgta tcggaacaaa ccaggttgat ctggatgcgg cggcaaagcg cgggatcccg        300
gtatttaacg caccgttctc aaatacgcgc tctgttgcgg agctggtgat ggcgaactg         360 ctgctgctat tgcgcggcgt gccggaagcc aatgctaaag cgcaccgtgg cgtgtggaac        420
aaactggcgg cgggttcttt tgaagcgcgc ggcaaaaagc tgggtatcat cggctacggt        480
catattggta cgcaattggg cattctggct gaatcgctgg gaatgtatgt ttacttttat        540
gatattgaaa ataaactgcc gctgggcaac gccactcagg tacagcatct ttctgacctg        600
ctgaatatga gcgatgtggt gagtctgcat gtaccagaga atccgtccac caaaaatatg        660
atgggcgcga agaaatttc actaatgaag cccggctcgc tgctgattaa tgcttcgcgc        720
ggtactgtgg tggatattcc ggcgctgtgt gatgcgctgg cgagcaaaca tctggcgggg       780
gcggcaatcg acgtattccc gacggaaccg gcgaccaata cgatccatt tacctctccg        840 ctgtgtgaat tcgacaacgt ccttctgacg ccacacattg gcggttcgac tcaggaagcg       900
caggagaata tcggcctgga agttgcgggt aaattgatca gtattctgaa caatggctca       960
acgctctctg cggtgaactt cccggaagtc tcgctgccac tgcacgttgg gcgtcgtctg      1020
```

```
atgcacatcc acgaaaaccg tccgggcgtg ctaactgcgc tgaacaaaat cttcgccgag      1080
cagggcgtca acatcgccgc gcaatatctg caaacttccg cccagatggg ttatgtggtt      1140
attgatattg aagccgacga agacgttgcc gaaaaagcgc tgcaggcaat gaaagctatt      1200
ccgggtacca ttcgcgcccg tctgctgtac taa                                   1233
```